(12) United States Patent
Shearer, Jr. et al.

(10) Patent No.: US 10,850,031 B2
(45) Date of Patent: *Dec. 1, 2020

(54) FLUID INJECTION SYSTEM HAVING VARIOUS SYSTEMS FOR CONTROLLING AN INJECTION PROCEDURE

(71) Applicant: BAYER HEALTHCARE LLC, Whippany, NJ (US)

(72) Inventors: John Shearer, Jr., Connellsville, PA (US); Christopher Scutt, Murrysville, PA (US); Walter Grumski, Pittsburgh, PA (US); Michael Spohn, Fenelton, PA (US); Jarrell T. McWilliams, Worthington, PA (US); Arlie D. Long, Monroeville, PA (US); Richard Morton, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 31 days.

This patent is subject to a terminal disclaimer.

(21) Appl. No.: 16/013,297

(22) Filed: Jun. 20, 2018

(65) Prior Publication Data

US 2018/0296754 A1  Oct. 18, 2018

Related U.S. Application Data

(62) Division of application No. 14/116,850, filed as application No. PCT/US2012/037491 on May 11, 2012, now Pat. No. 10,022,493.

(Continued)

(51) Int. Cl.
*A61M 5/168* (2006.01)
*A61M 5/00* (2006.01)
*A61M 5/145* (2006.01)

(52) U.S. Cl.
CPC .......... *A61M 5/16831* (2013.01); *A61M 5/00* (2013.01); *A61M 5/007* (2013.01);
(Continued)

(58) Field of Classification Search
CPC .. A61M 5/007; A61M 5/008; A61M 5/16831; A61M 5/1452; A61M 5/14546; A61M 2005/14553; A61M 2205/215
See application file for complete search history.

(56) References Cited

U.S. PATENT DOCUMENTS 4,869,266 A   9/1989  Taylor et al.
5,242,408 A   9/1993  Jhuboo et al.
(Continued)

FOREIGN PATENT DOCUMENTS

EP   1829576 A1   9/2007
EP   2345441 A1   7/2011
(Continued)

OTHER PUBLICATIONS

The Supplementary European Search Report dated Nov. 5, 2014 from corresponding EP Application No. 12782172.6.
(Continued)

*Primary Examiner* — Manuel A Mendez
*Assistant Examiner* — Justin L Zamory
(74) *Attorney, Agent, or Firm* — David Schramm; Joseph L. Kent; James R. Stevenson

(57) ABSTRACT

A fluid injection system that includes an injector head having a syringe for delivering a fluid to a patient; a mounting structure pivotally connected to the injector head and configured to support the injector head above a surface; and a control system operationally coupled to the injector head for controlling an injection procedure is disclosed. The fluid injection system is provided with various sensors to control various aspects of the fluid injection system, such as (Continued)

the establishment of a reference plane, the determination of a tilt angle of the injector head, and the determination of a temperature of an actuation system of the injector head.

16 Claims, 30 Drawing Sheets

Related U.S. Application Data

(60) Provisional application No. 61/485,238, filed on May 12, 2011.

(52) U.S. Cl.
CPC ............. *A61M 5/14546* (2013.01); *A61M 2005/14553* (2013.01); *A61M 2205/215* (2013.01); *A61M 2205/50* (2013.01); *A61M 2205/502* (2013.01)

(56) References Cited

U.S. PATENT DOCUMENTS

| | | | |
|---|---|---|---|
| 5,254,096 A | 10/1993 | Rondelet et al. | |
| 5,383,858 A | 1/1995 | Reilly et al. | |
| 5,460,609 A | 10/1995 | O'Donnell | |
| 5,566,098 A | 10/1996 | Lucente et al. | |
| 5,573,515 A | 11/1996 | Wilson et al. | |
| 5,800,397 A | 9/1998 | Wilson et al. | |
| 5,868,710 A * | 2/1999 | Battiato ............ | A61M 5/14546 604/123 |
| 5,925,022 A | 7/1999 | Battiato et al. | |
| 6,004,285 A | 12/1999 | Sugahara | |
| 6,004,292 A | 12/1999 | Battiato et al. | |
| 6,159,183 A | 12/2000 | Neer et al. | |
| 6,221,045 B1 * | 4/2001 | Duchon ................. | A61B 6/481 128/DIG. 1 |
| 6,254,572 B1 | 7/2001 | Knipfer et al. | |
| 6,554,791 B1 | 4/2003 | Cartledge et al. | |
| 6,658,276 B2 | 12/2003 | Kianl et al. | |
| 6,869,413 B2 | 3/2005 | Langley et al. | |
| 6,942,637 B2 | 9/2005 | Cartledge et al. | |
| 6,969,370 B2 | 11/2005 | Langley et al. | |
| 6,997,905 B2 | 2/2006 | Gillespie et al. | |
| 6,997,906 B2 | 2/2006 | Langley et al. | |
| 7,018,361 B2 | 3/2006 | Gillespie et al. | |
| 7,201,734 B2 | 4/2007 | Hickle | |
| 7,308,894 B2 | 12/2007 | Hickle | |
| 7,311,691 B2 | 12/2007 | Cartledge et al. | |
| 7,326,189 B2 | 2/2008 | Mori | |
| 7,334,639 B2 | 2/2008 | Svoboda | |
| 7,338,260 B2 | 3/2008 | Brundle et al. | |
| 7,530,949 B2 | 5/2009 | Ali et al. | |
| 7,549,977 B2 | 6/2009 | Schriver et al. | |
| 7,553,294 B2 | 6/2009 | Lazzaro et al. | |
| 7,556,619 B2 | 7/2009 | Spohn et al. | |
| 7,563,249 B2 | 7/2009 | Schriver et al. | |
| 7,608,060 B2 | 10/2009 | Gillespie, Jr. et al. | |
| 7,611,503 B2 | 11/2009 | Spohn et al. | |
| 7,699,815 B2 | 4/2010 | Langley et al. | |
| 7,713,241 B2 | 5/2010 | Cartledge et al. | |
| 7,771,389 B2 | 8/2010 | Grispo et al. | |
| 7,806,891 B2 | 10/2010 | Nowlin et al. | |
| 7,862,534 B2 | 1/2011 | Quirico et al. | |
| 7,922,692 B2 | 4/2011 | Francis | |
| 7,927,307 B2 | 4/2011 | D'Antonio et al. | |
| 8,133,203 B2 | 3/2012 | Hack | |
| 8,172,796 B2 | 5/2012 | Schriver et al. | |
| 2003/0216692 A1 | 11/2003 | Fago et al. | |
| 2004/0015075 A1 | 1/2004 | Kimchy et al. | |
| 2004/0054318 A1 | 3/2004 | Langley et al. | |
| 2004/0054319 A1 | 3/2004 | Langley et al. | |
| 2004/0054328 A1 | 3/2004 | Langley et al. | |
| 2004/0097873 A1 | 5/2004 | Langley et al. | |
| 2004/0122355 A1 | 6/2004 | Langley et al. | |
| 2005/0027238 A1 | 2/2005 | Fago et al. | |
| 2005/0171487 A1 | 8/2005 | Haury et al. | |
| 2005/0182322 A1 | 8/2005 | Grispo | |
| 2005/0182323 A1 | 8/2005 | Grispo et al. | |
| 2006/0079768 A1 | 4/2006 | Small et al. | |
| 2006/0079842 A1 | 4/2006 | Small et al. | |
| 2006/0079843 A1 | 4/2006 | Brooks et al. | |
| 2006/0259267 A1 | 11/2006 | Narayanasamy | |
| 2007/0100282 A1 | 5/2007 | Small et al. | |
| 2007/0213658 A1 | 9/2007 | Hickle | |
| 2008/0021379 A1 | 1/2008 | Hickle | |
| 2008/0071218 A1 | 3/2008 | D'Antonio et al. | |
| 2008/0086087 A1 | 4/2008 | Spohn et al. | |
| 2008/0216692 A1 | 9/2008 | Zaher et al. | |
| 2009/0149743 A1 | 6/2009 | Barron et al. | |
| 2009/0221914 A1 | 9/2009 | Barrett et al. | |
| 2009/0254037 A1 | 10/2009 | Bryant, Jr. et al. | |
| 2010/0036384 A1 | 2/2010 | Gorek et al. | |
| 2010/0174181 A1 | 7/2010 | Nemoto | |
| 2010/0217121 A1 | 8/2010 | Nemoto | |
| 2010/0256561 A1 | 10/2010 | Gillespie, Jr. et al. | |
| 2010/0256562 A1 | 10/2010 | Cartledge et al. | |
| 2010/0275256 A1 | 10/2010 | Mathew et al. | |
| 2010/0293496 A1 | 11/2010 | Lafferty et al. | |
| 2010/0312039 A1 | 12/2010 | Quirico et al. | |
| 2011/0028818 A1 | 2/2011 | Moberg et al. | |
| 2012/0123257 A1 | 5/2012 | Stokes, Jr. et al. | |

FOREIGN PATENT DOCUMENTS

| | | |
|---|---|---|
| JP | S5186974 U | 7/1976 |
| JP | 2008136786 A | 6/2008 |
| WO | 0010629 A1 | 3/2000 |
| WO | 2004058332 A2 | 7/2004 |
| WO | 2006068171 A1 | 6/2006 |
| WO | 2007033103 A1 | 3/2007 |
| WO | 2008070269 A2 | 6/2008 |
| WO | 2010019456 A1 | 2/2010 |
| WO | 2011011346 A1 | 1/2011 |

OTHER PUBLICATIONS

International Preliminary Report on Patentability International Application No. PCT/US2012/037491, dated Nov. 12, 2013.

International Search Report with Written Opinion for International Application No. PCT/US2012/037491 dated Aug. 17, 2012.

\* cited by examiner

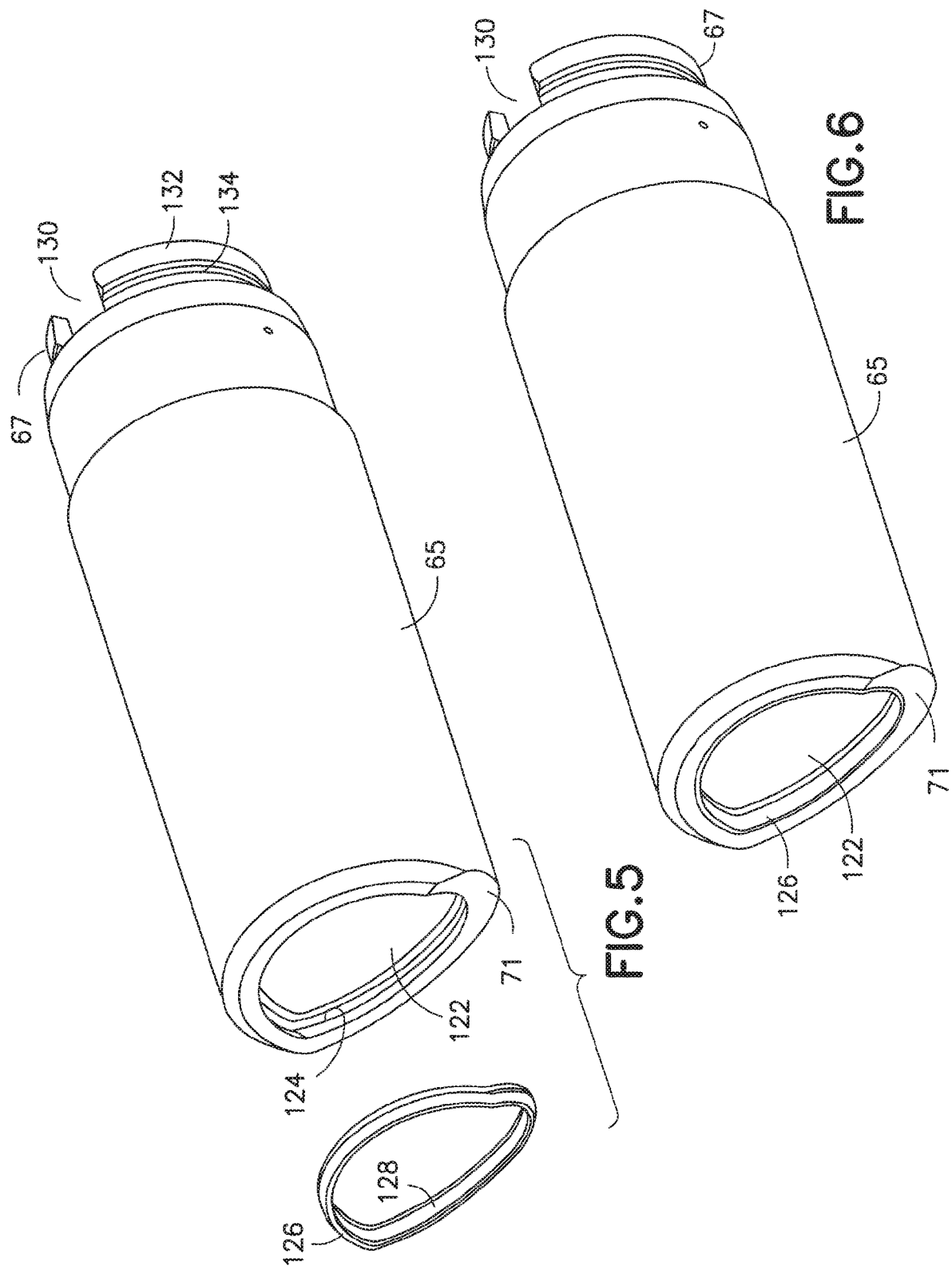

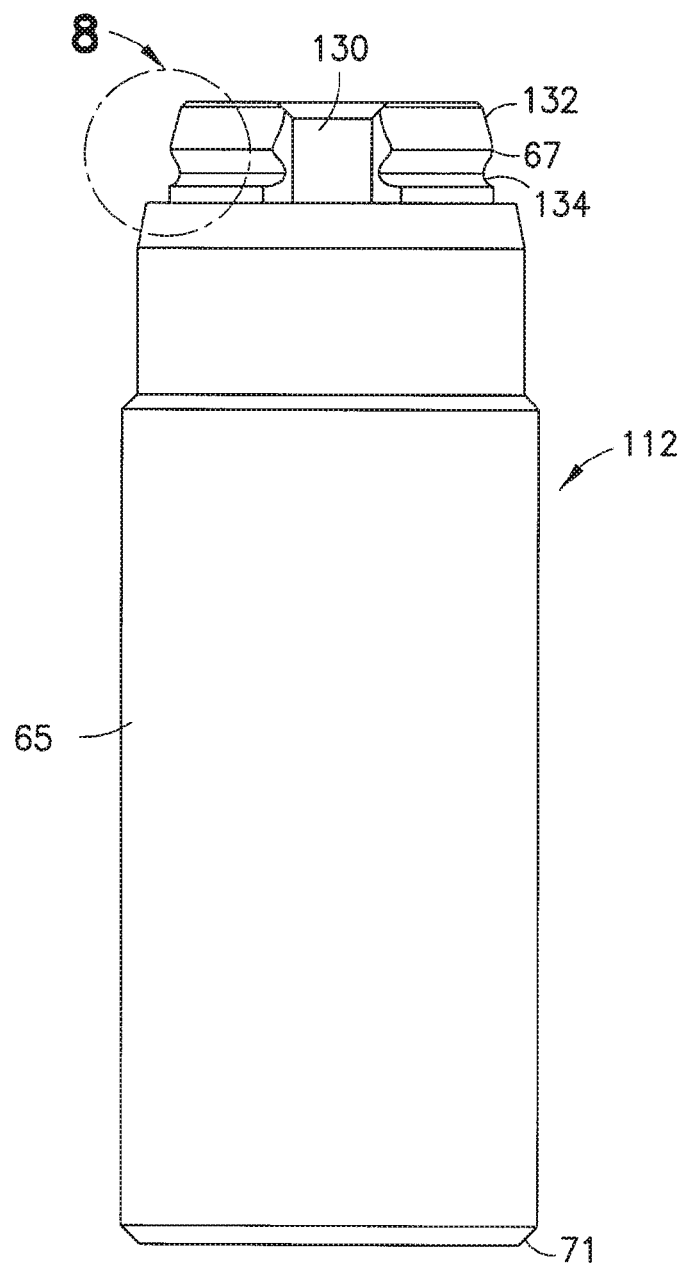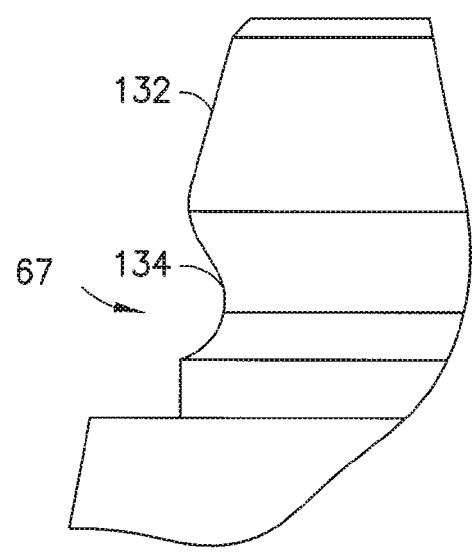
FIG.7
FIG.8

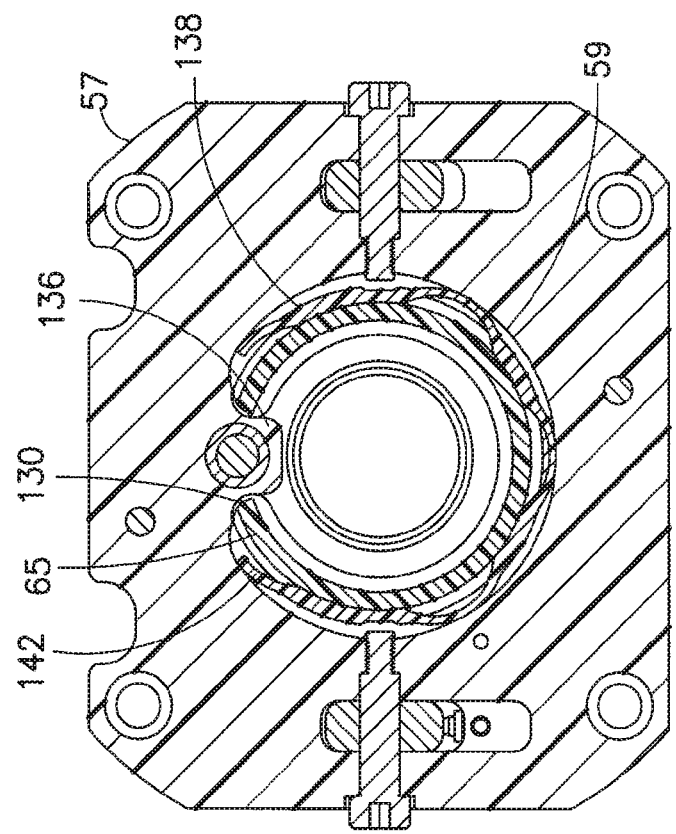
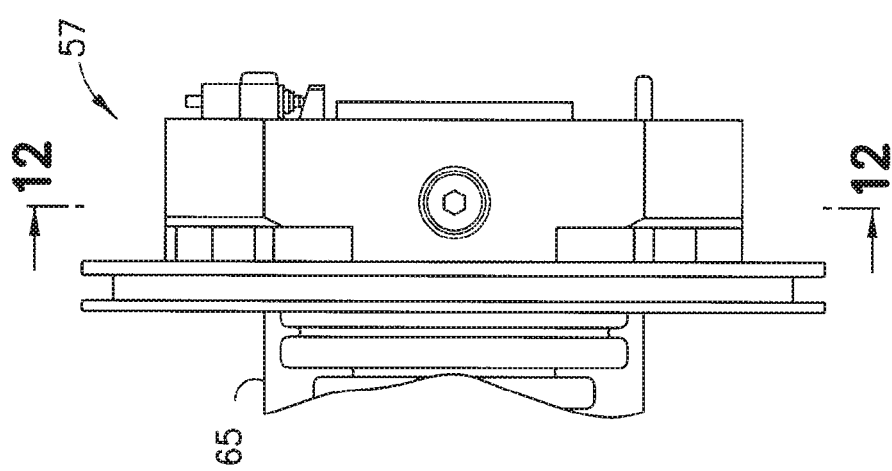
FIG. 12
FIG. 11

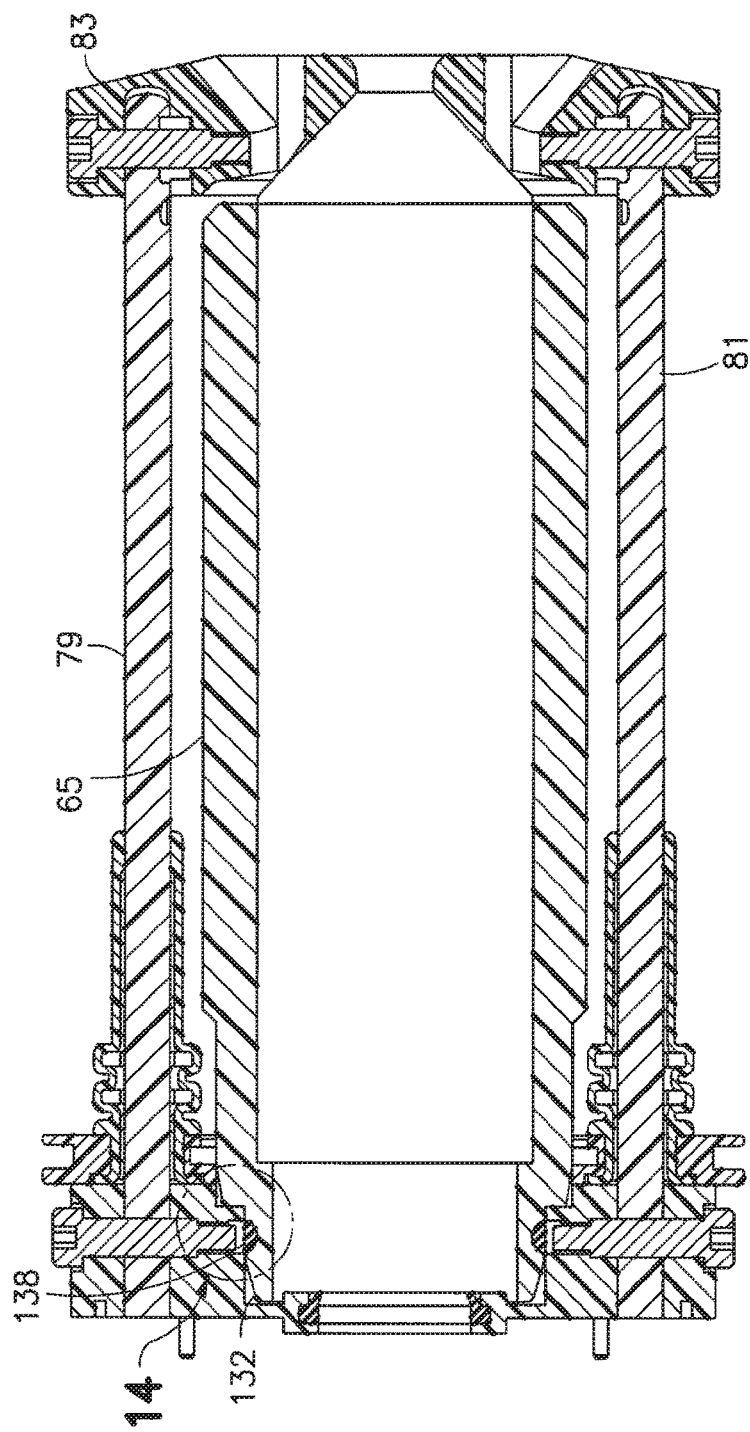
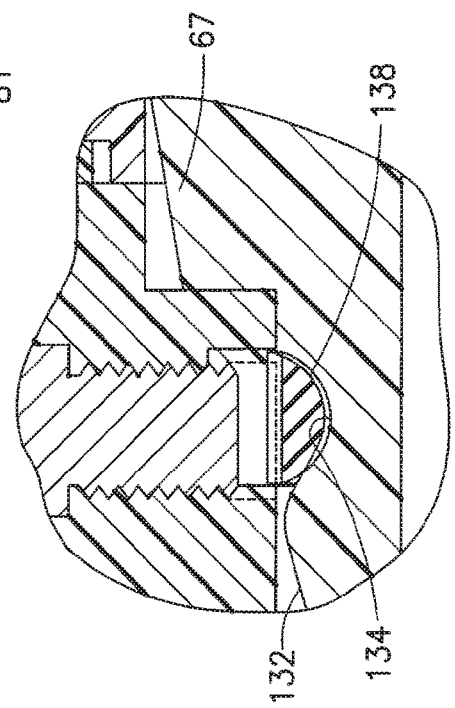
FIG. 13
FIG. 14

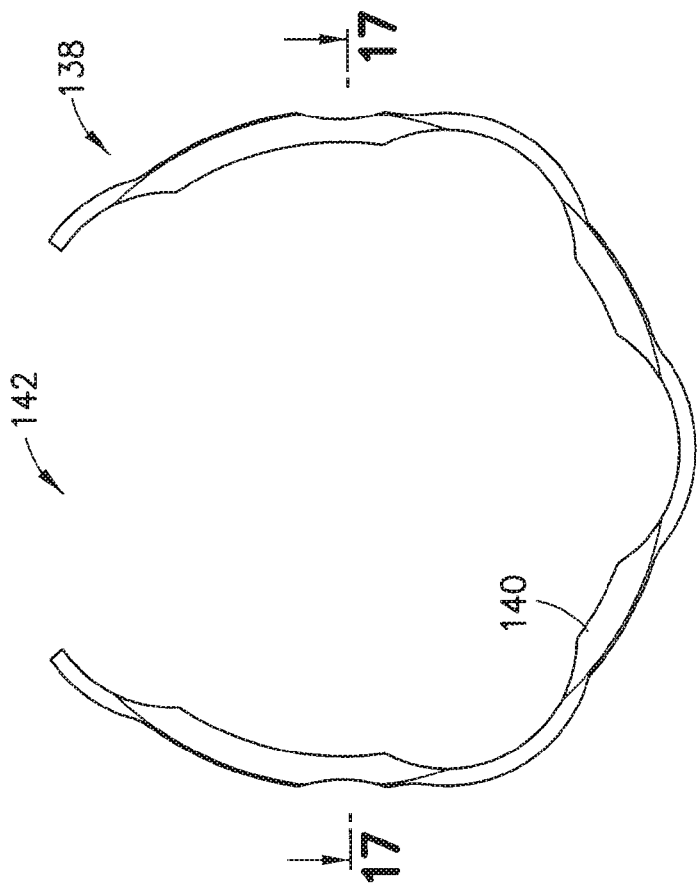
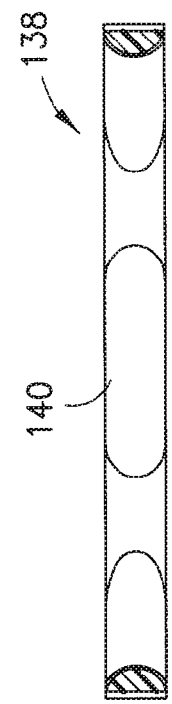
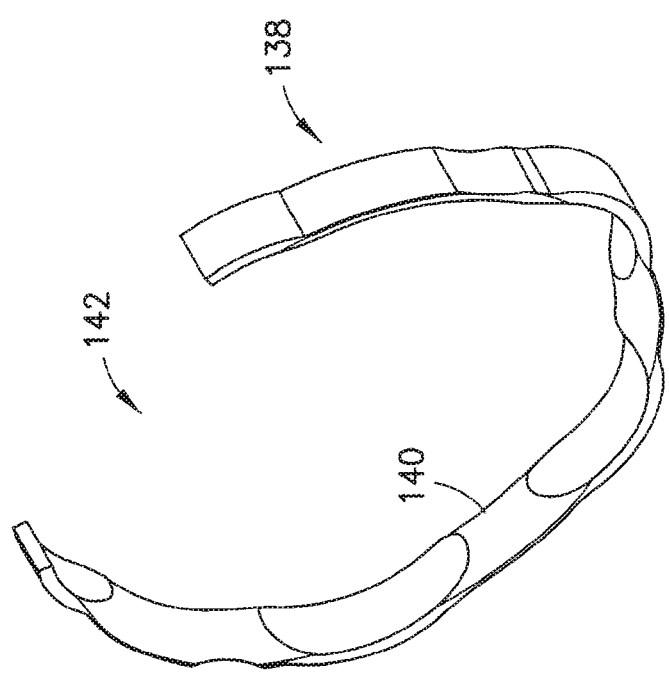
FIG. 16
FIG. 17
FIG. 15

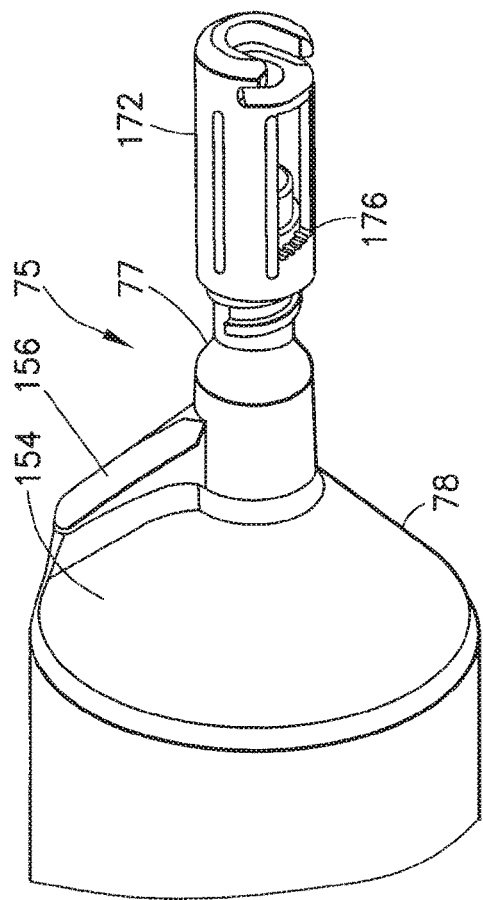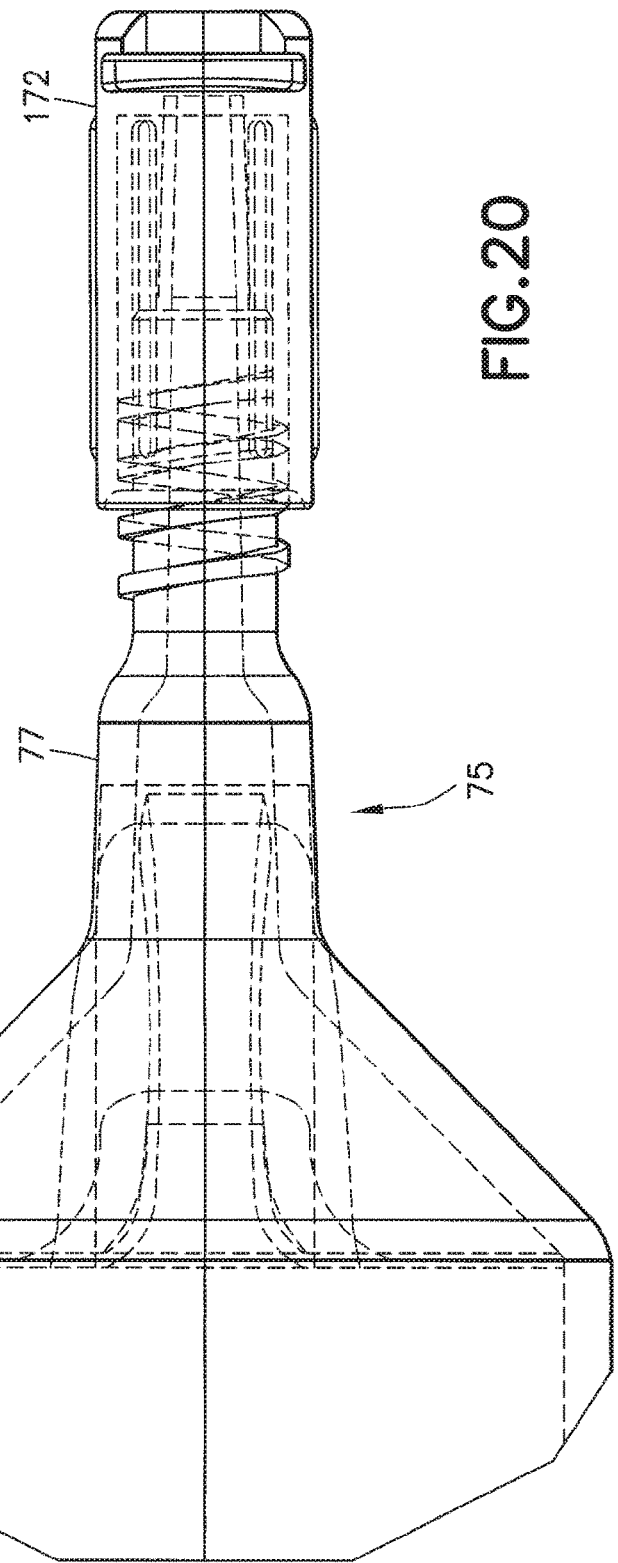

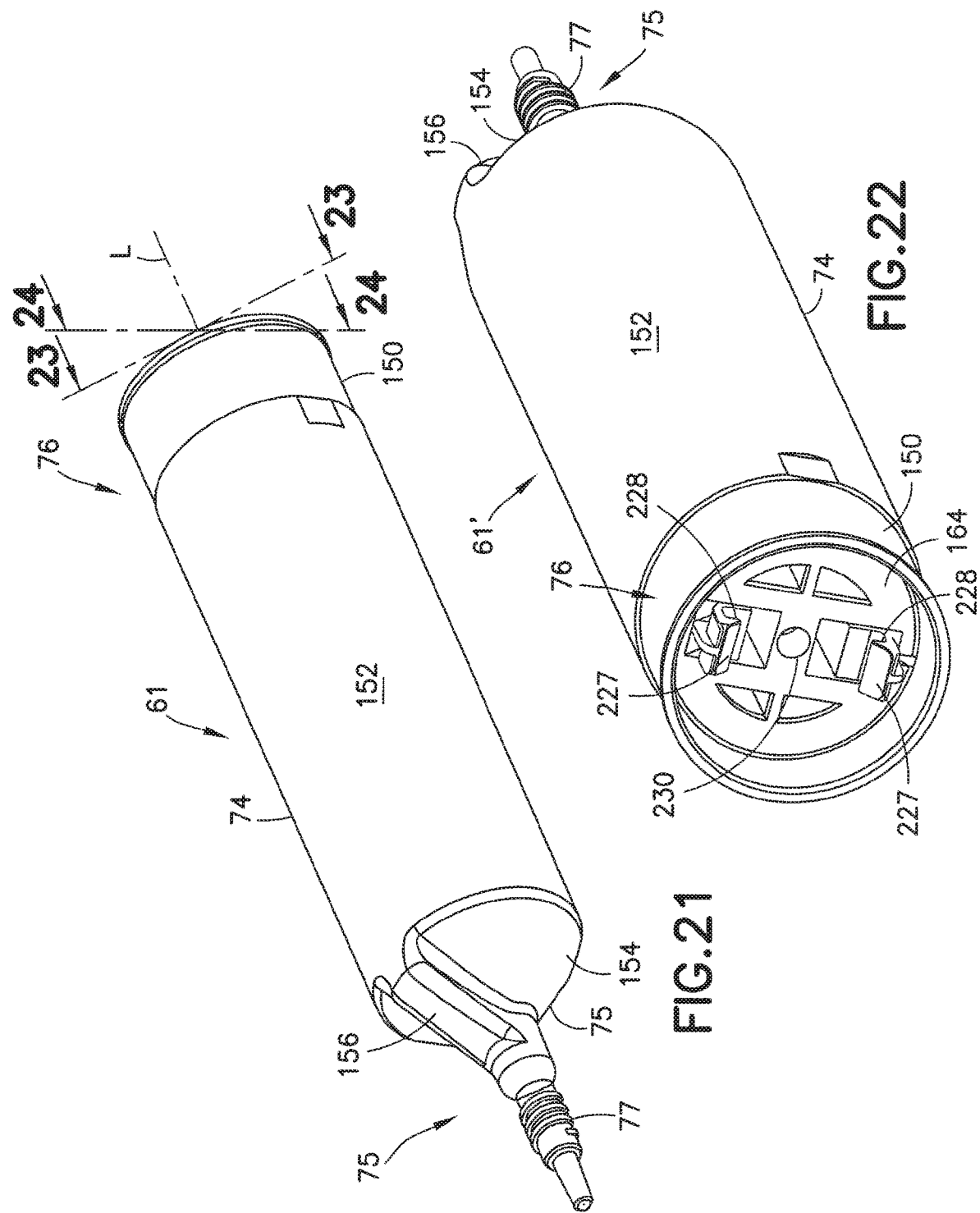

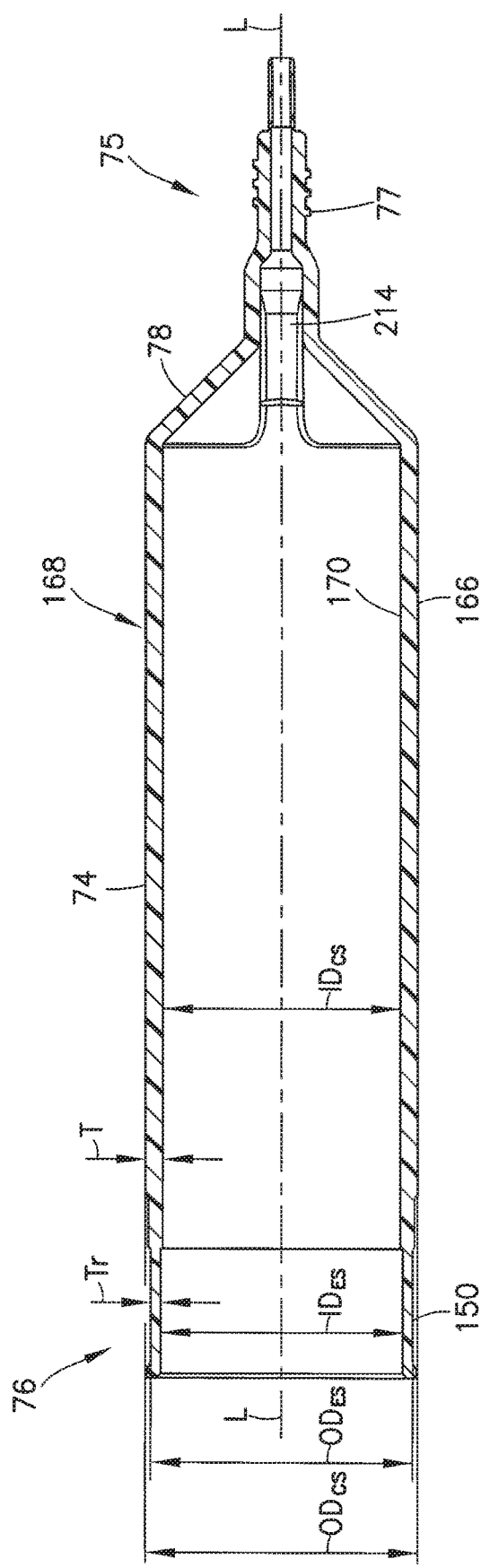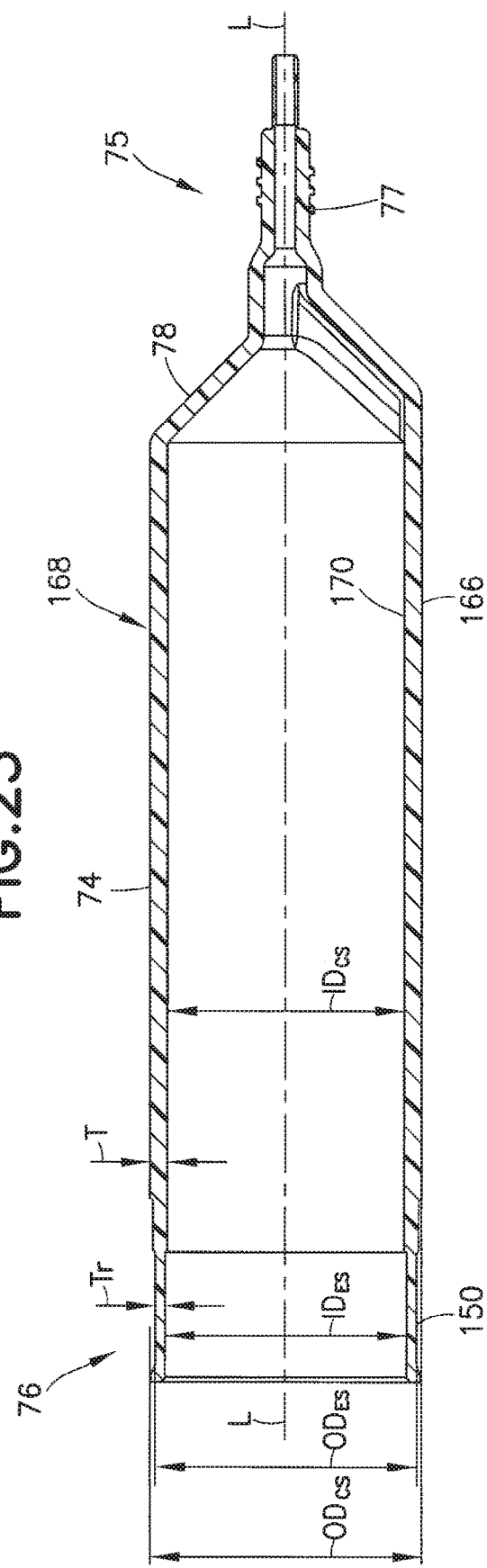

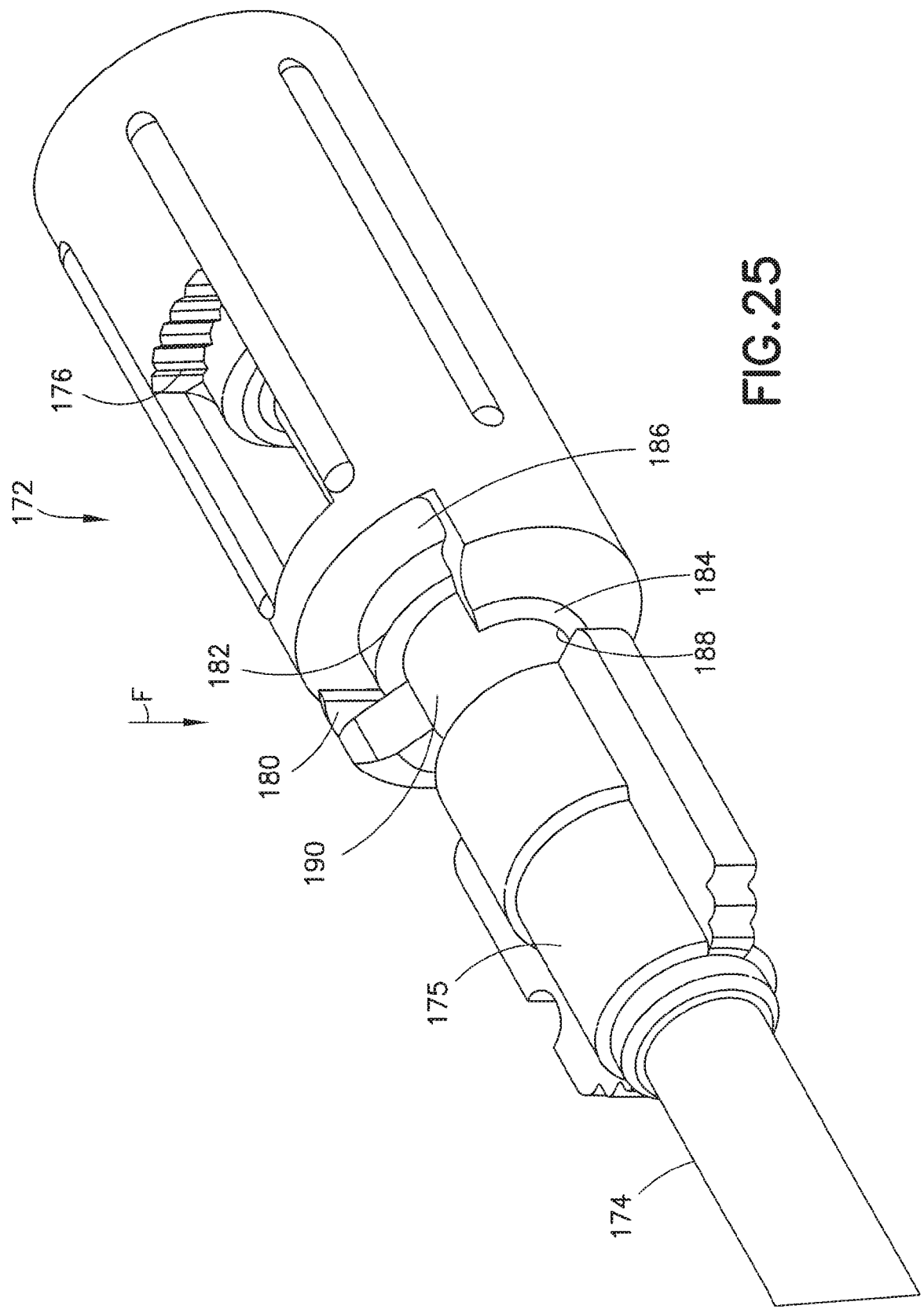

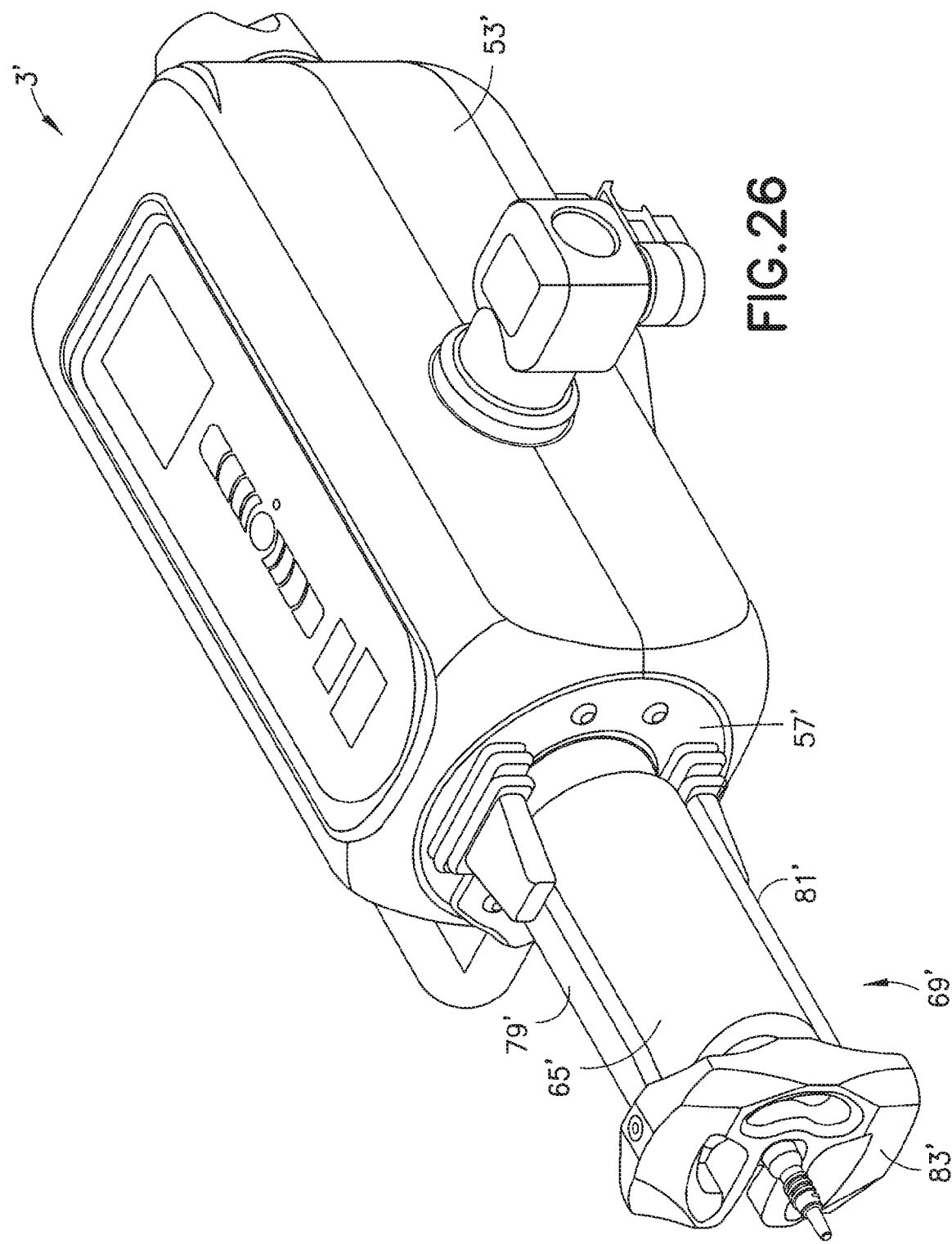

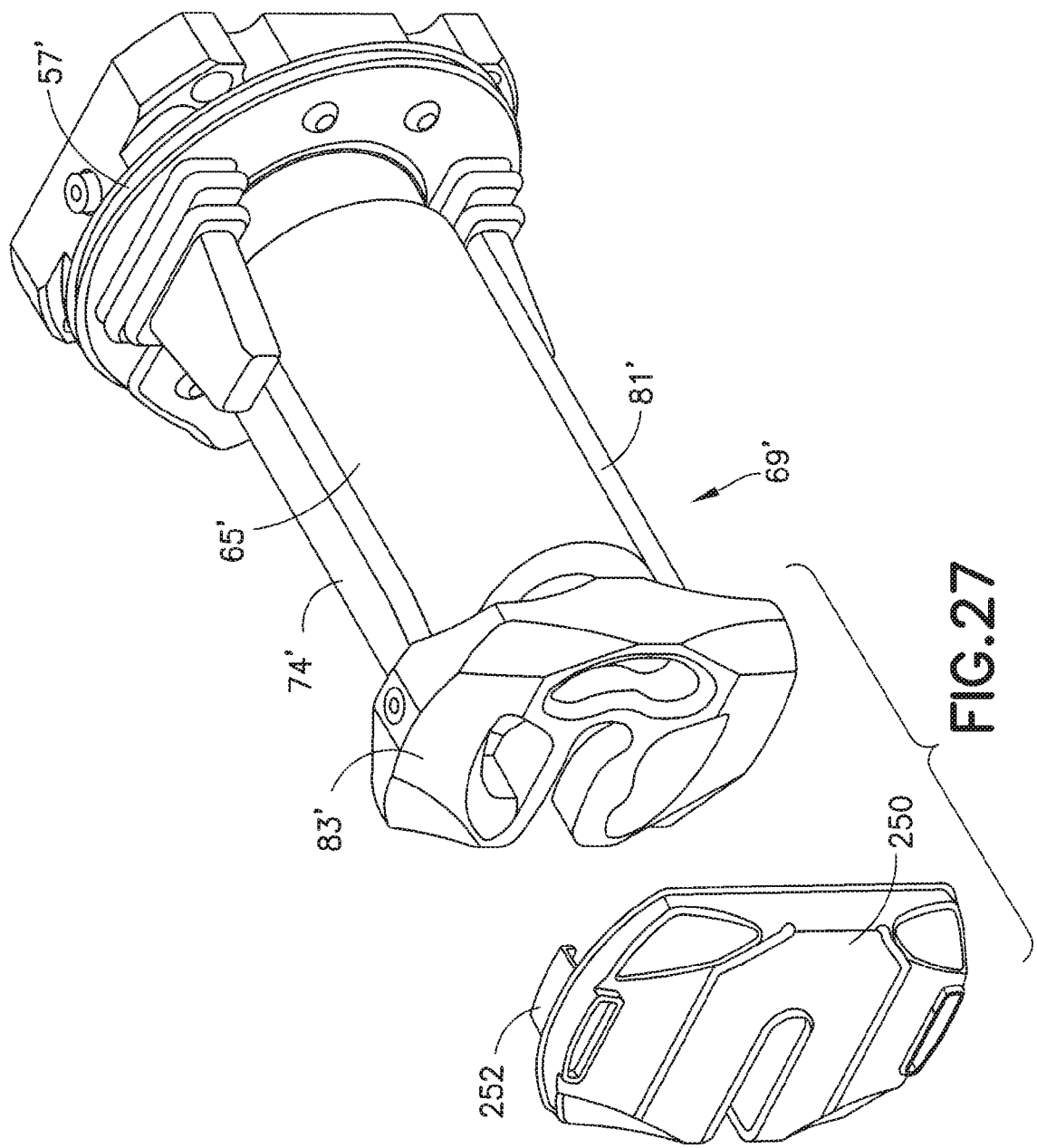

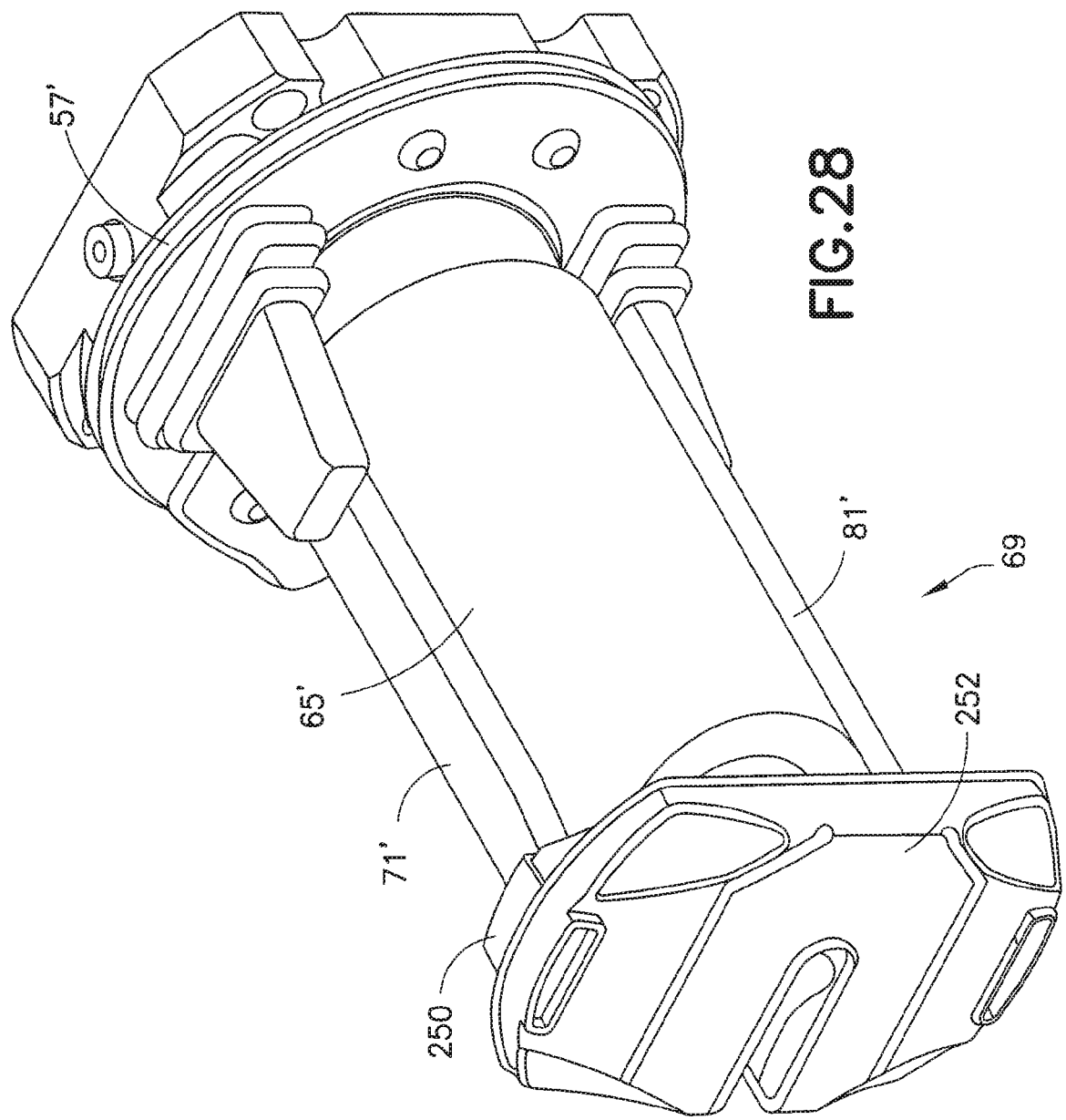

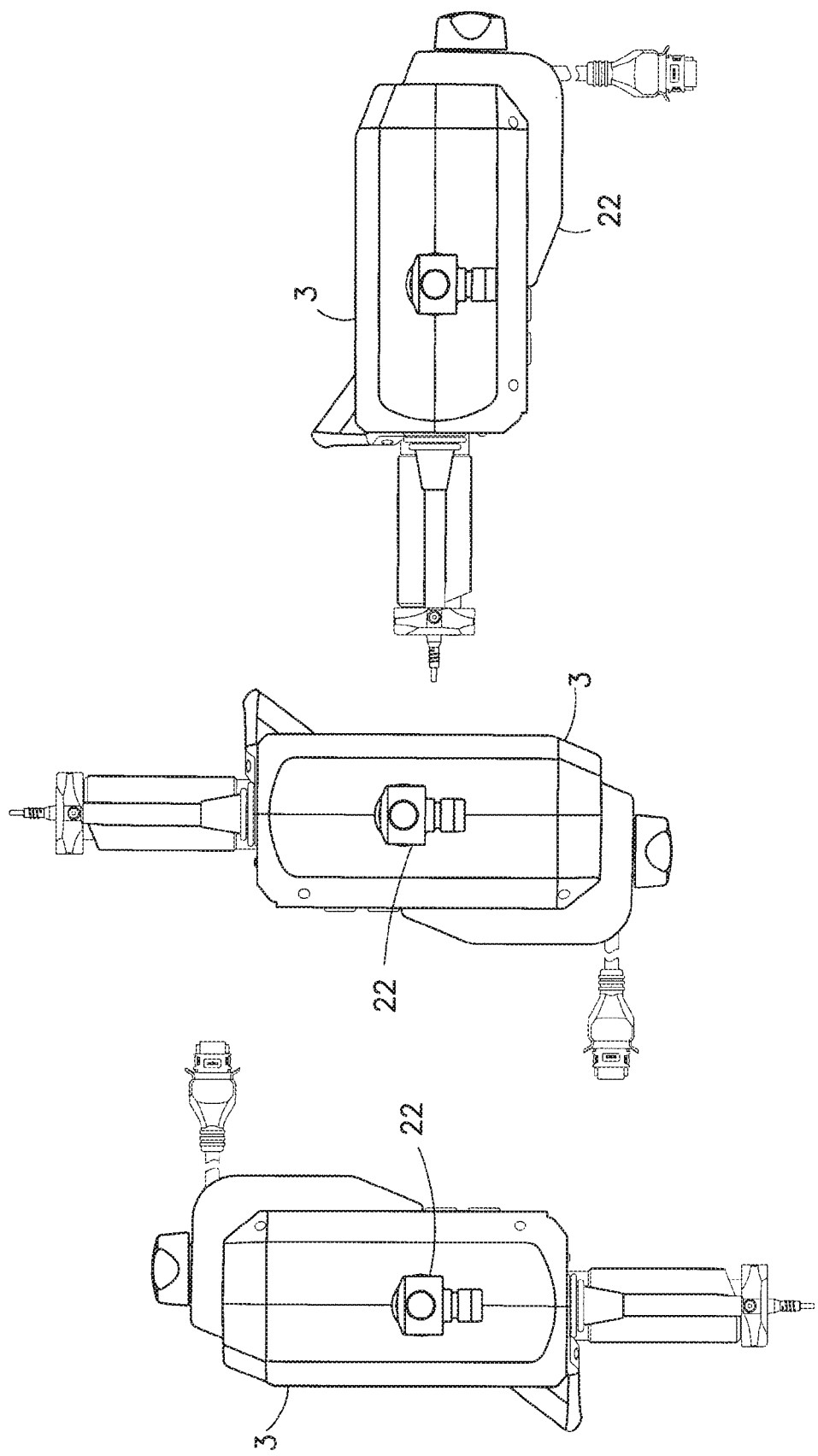

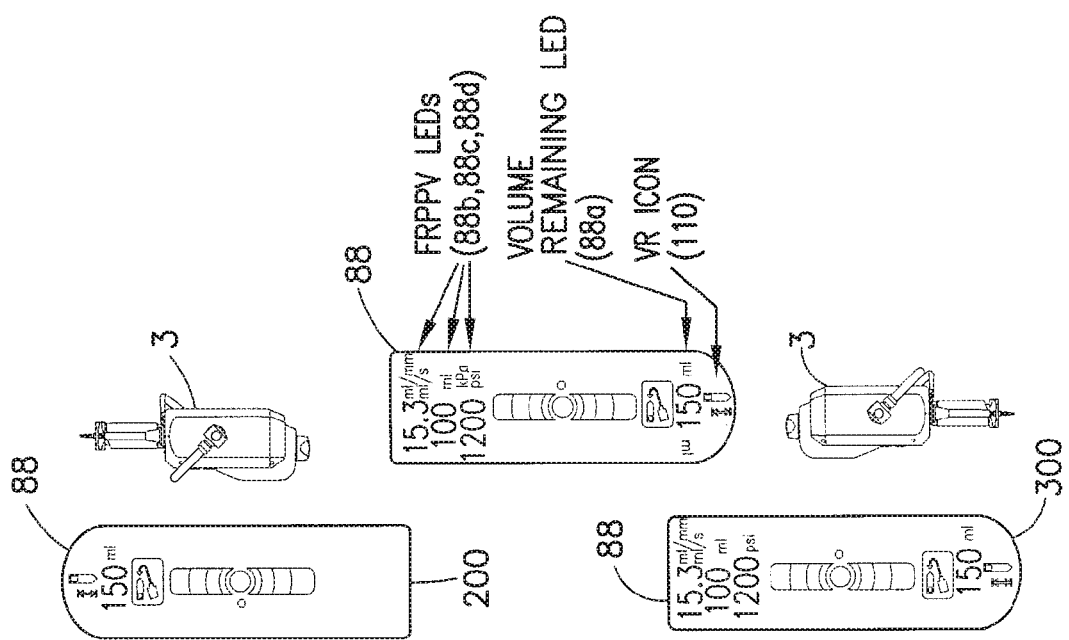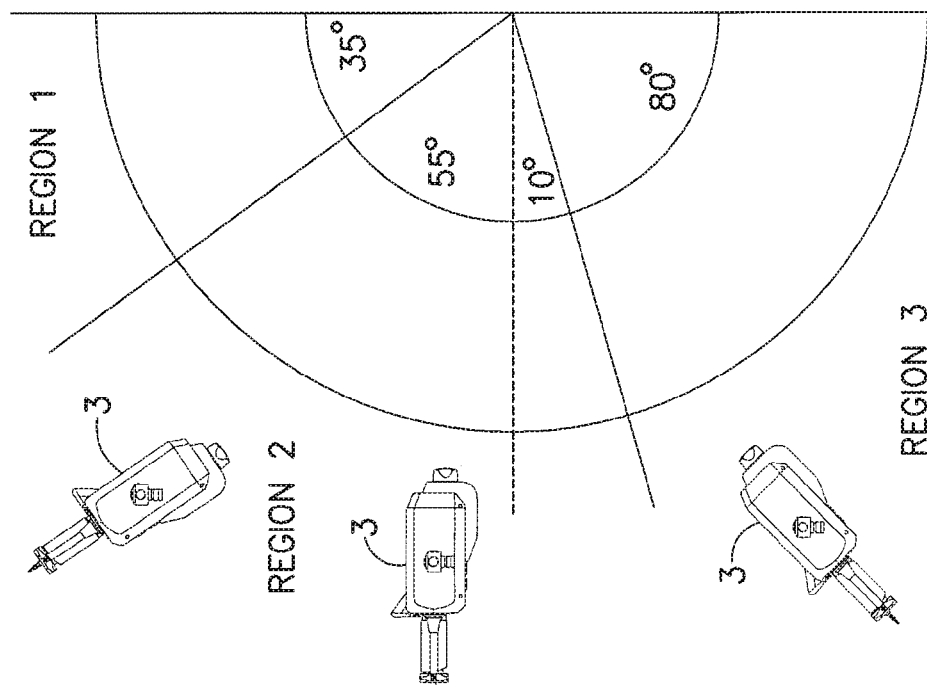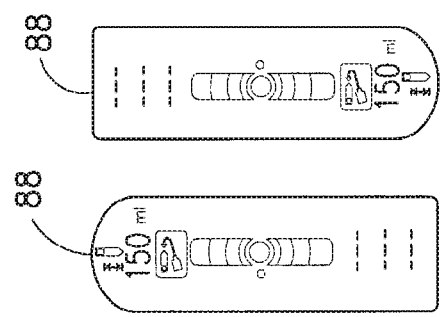
FIG.40

FLUID INJECTION SYSTEM HAVING VARIOUS SYSTEMS FOR CONTROLLING AN INJECTION PROCEDURE

CROSS REFERENCE TO RELATED APPLICATIONS

This application is a divisional application of U.S. Serial application Ser. No. 14/116,850, filed Nov. 11, 2013, now U.S. Pat. No. 10,022,493, issued Jul. 17, 2018, which is a 371 national phase application of PCT International Application No. PCT/US2012/37491, filed on May 11, 2012, and designating the United States of America, which claims the benefit of U.S. Provisional Application Ser. No. 61/485,238, filed on May 12, 2011, the contents of which are incorporated herein by reference.

BACKGROUND OF THE INVENTION

Field of the Invention

The devices of the present disclosure relate generally to fluid injection systems for supplying fluids during medical and therapeutic procedures and, more specifically, for controlling the fluid supplied during an angiographic injection procedure.

Description of Related Art

In many medical diagnostic and therapeutic procedures, a physician or other person injects a patient with a fluid. In recent years, a number of injector-actuated syringes and powered injectors for pressurized injection of fluids, such as contrast media, have been developed for use in procedures such as angiography, computed tomography, ultrasound, and NMR/MRI. In general, these powered injectors are designed to deliver a preset amount of contrast media at a preset flow rate. Angiography is used generally in the diagnosis and therapeutic treatment of abnormalities in blood vessels. In an angiographic procedure, a radiographic image of vascular structure is obtained through the use of a radiographic contrast medium, sometimes referred to simply as contrast, injected through a catheter. The vascular structures are injected and filled with contrast. X-rays passing through the region of interest are absorbed by the contrast, causing a radiographic image of the blood vessels. The resulting images can be displayed on, for example, a monitor and recorded.

In a typical angiographic procedure, a physician places a catheter into a vein or artery. The catheter is connected to either a manual or to an automatic contrast injection mechanism. A typical manual contrast injection mechanism includes a syringe in fluid connection with a catheter. The fluid path also includes, for example, a source of contrast fluid, a source of saline, and a pressure transducer to measure patient blood pressure. In a typical system, the source of contrast is connected to the fluid path via a valve, for example, a three-way stopcock. The source of saline and pressure transducer P may also be connected to the fluid path via additional valves. The operator of the manual system manually controls the syringe and each of the valves to draw saline or contrast into the syringe and to inject the saline or contrast into the patient through the catheter connection.

The operator of the syringe may adjust the flow rate, or simply known as flow, and volume of injection by altering the force applied to the plunger of the syringe. Manual sources of fluid pressure and flow used in medical applications, such as syringes and manifolds thus typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast material and a fixed rate of injection. In many systems, there is no interactive control between the operator and the powered injector, except to start or stop the injection. A change in flow rate in such systems occurs by stopping the machine and resetting the parameters. Automation of angiographic procedures using powered injectors is discussed, for example, in U.S. Pat. Nos. 5,460,609, 5,573,515, and 5,800,397.

U.S. Pat. No. 5,800,397, for example, discloses an angiographic injector system having high pressure and low pressure systems. The high pressure system includes a motor-driven injector pump to deliver radiographic contrast material under high pressure to a catheter. The low pressure system includes, among other things, a pressure transducer to measure blood pressure and a pump to deliver a saline solution to the patient as well as to aspirate waste fluid. A manifold is connected to the syringe pump, the low pressure system, and the patient catheter. A flow valve associated with the manifold is normally maintained in a first state connecting the low pressure system to the catheter through the manifold, and disconnecting the high pressure system from the catheter and the low pressure system. When pressure from the syringe pump reaches a predetermined and set level, the valve switches to a second state connecting the high pressure system/syringe pump to the catheter, while disconnecting the low pressure system from the catheter and from the high pressure system. However, the arrangement of the system components of U.S. Pat. No. 5,800,397 results in relatively large amounts of wasted contrast and/or undesirable injection of an excessive amount of contrast when the low pressure, typical saline system, is used.

Unlike manual injection systems, however, there is little if any feedback to the operator of system pressure in the systems disclosed in the U.S. patents identified previously. There are potential advantages to such feedback. In the use of a manual syringe, for example, excessive back pressure on the syringe plunger can provide evidence of occlusion of the fluid path.

While manual and automated injectors are known in the medical field, a need generally exists for improved fluid injection systems adapted for use in medical diagnostic and therapeutic procedures where fluids are supplied to a patient during the procedure. A specific need generally exists for an improved fluid injection system for use in fluid injection procedures, such as angiography. Moreover, a continuing need exists in the medical field to generally improve upon known medical devices and systems used to supply fluids to patients during medical procedures, such as angiography, computed tomography, ultrasound, and NMR/MRI.

SUMMARY

According to one aspect of the device of the present disclosure, provided is a fluid injection system that includes: an injector head for delivering a fluid to a patient; a mounting structure pivotally connected to the injector head and configured to mount the injector head to an examination table; a reference plane sensor positioned within the injector head for determining an orientation of the injector head relative to the mounting structure; and a control system operationally coupled to the injector head and the reference plane sensor for controlling an injection procedure. The control system is configured to receive an input from the reference plane sensor to establish a reference plane with respect to a floor surface and alert a user if an offset that is detrimental to air management exists between the reference plane and the floor surface.

The control system may be operationally coupled to a display unit having a graphical user interface. The user may be alerted that an offset exists between the reference plane and the floor surface by a message appearing on the graphical user interface of the display unit. The display unit may be mounted to a rail of the examination table by an additional mounting structure.

The mounting structure may include a clamping mechanism removably coupled to a rail of the examination table, a pole extending from the clamping mechanism above the examination table, and a support arm having a first end pivotally coupled to the pole and a second end pivotally coupled to the injector head. If the user is alerted that an offset exists between the reference plane and the floor surface, the user may reposition the injector head by rotating the injector head around the second end of the support arm until the reference plane sensor establishes a new reference plane that is parallel to the floor surface.

Desirably, a reference plane sensor is a 3-axis accelerometer. In addition, the injector head may include a housing having a display on a top portion thereof.

According to another aspect of the device of the present disclosure, provided is a fluid injection system that includes: an injector head for delivering a fluid to a patient; a mounting structure having a support arm with a first end coupled to a generally vertically extending mounting pole and a second end pivotally coupled to the injector head by a pivoting knuckle; a display for displaying information regarding the activities and state of operation of the injector head; a potentiometer positioned within the knuckle for generating a tilt angle signal indicative of an angle of tilt of the injector head relative to the mounting pole; and a control circuit connected to the injector head, the potentiometer, and the display for controlling delivery of the fluid to the patient, for generating display information and delivering the display information to the display, and for receiving the tilt angle signal from the potentiometer. The display is responsive to the tilt angle signal to display the display information in a first orientation in response to a first range of values of the tilt angle signal, and to display the display information in a second orientation in response to a second range of values of the tilt angle signal.

The display may be positioned on a housing of the injector head. The display may be configured to display information regarding volume remaining, flow rate, pressure, programmed volume, or any combination thereof. The control system may be operationally coupled to an additional display having a graphical user interface. The additional display may be located remotely from the injector head. The additional display may be pivotally mounted to the mounting pole by an additional support arm. The control system may be configured to prevent an injection if the tilt angle signal is received from the potentiometer and indicates that the injector head is tilted upwardly.

According to yet another aspect of the device of the present disclosure, provided is a fluid injection system that includes: an injector head for delivering a fluid to a patient; a plurality of sensors positioned within the injector head for generating signals indicative of the status of the injector head; a control system operationally coupled to the injector head and the plurality of sensors for controlling an injection procedure; and a display unit operationally coupled to the control system. Based on the signals generated by the plurality of sensors, the control system generates a list of actions on the display unit that must be completed by a user before the injector head can be armed to perform the injection procedure. In addition, as one of the plurality of sensors determines that the user has completed an action from the list of actions, the action may be removed from the list of actions on the display unit. The list of actions may include at least one of the following actions: load syringe, engage drop front, advance plunger, rotate injector head down to arm, rotate syringe and remove, disconnect patient, flow rate reduced, calibration needed, rotate head up and purge, injection complete, procedure halt—display touch, procedure halt—head touch, procedure halt—start switch, procedure halt—ISI, and procedure halt—low volume.

A mounting structure may be pivotally connected to the injector head and configured to support the injector head. The mounting structure includes: a mobile base positioned on the floor; a pole extending from the mobile base above the floor; and a first support arm having a first end pivotally coupled to the pole and a second end pivotally coupled to the injector head. The mounting structure may further include a second support arm having a first end pivotally coupled to the pole and a second end pivotally coupled to the display unit. The display unit may be a graphical user interface for allowing a user to control an injection procedure and for displaying the list of actions.

The injector head may include a housing having a display on a top portion thereof. The housing of the injector head may include a handle extending therefrom for allowing a user to manipulate the injector head.

According to still another aspect of the device of the present disclosure, provided is a fluid injection system that includes an injector head for delivering a fluid to a patient. The injector head includes: a housing; a mechanical interface on a front face of the housing for receiving a disposable syringe; a piston positioned within the housing for connecting to a plunger of the disposable syringe; and an actuation system positioned within the housing for moving the piston. The fluid injection system also includes: at least one temperature sensor positioned in the vicinity of the actuation system within the housing of the injector head for generating signals indicative of the temperature of the actuation system; and a control system operationally coupled to the injector head and the at least one temperature sensor for controlling an injection procedure. The control system inhibits operation of the actuation system if a temperature determined by the at least one temperature sensor exceeds a predefined threshold level.

The actuation system may include: a gear train and linear ball screw; a brushless DC motor coupled to the gear train and linear ball screw; and a motor amplifier operationally coupled to the motor. The control system may be operationally coupled to a display unit having a graphical user interface. A user may be alerted that the temperature determined by the at least one temperature sensor exceeds the predefined threshold level by a message appearing on the graphical user interface of the display unit.

According to yet another aspect of the device of the present disclosure, provided is a syringe for use with each of the above-described fluid injection systems. The syringe includes a body having a distal end and a proximal end and a center section therebetween. The distal end includes an injection section having a conical portion that extends and tapers from the center section to an injection neck forming a discharge outlet and the proximal end includes a radial expansion section having a reduced wall thickness such that an inner diameter of the radial expansion section is larger than an inner diameter of the center section and the outer diameter of the radial expansion section is smaller than an outer diameter of the center section. The syringe also includes a plunger movably disposed in the body and having a coupling end. The plunger is substantially seated in the radial expansion section in a pre-use state of the syringe. In addition, an alignment flange is formed on the conical portion and extends the distance between the center section and the injection neck. The alignment flange is generally rectangular in shape and defines an internal hollow area therein in fluid communication with the interior of the body.

These and other features and characteristics of the device of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the device of the present disclosure. As used in the specification and the claims, the singular form of "a", "an", and "the" include plural referents unless the context clearly dictates otherwise.

BRIEF DESCRIPTION OF THE DRAWINGS

FIG. 5 is an exploded perspective view of a pressure jacket and wiper seal for use therewith in accordance with the device of the present disclosure;

FIG. 6 is an assembled perspective view of the pressure jacket and wiper seal of FIG. 5;

FIG. 7 is a top plan view of the pressure jacket of FIG. 5;

FIG. 8 is a portion of the pressure jacket of FIG. 7 enlarged for magnification purposes;

FIG. 11 is a side plan view of a faceplate of the injector head in accordance with the device of the present disclosure;

FIG. 12 is a cross-sectional view of the faceplate of FIG. 11 taken along line 12-12;

FIG. 13 is a cross-sectional view of the pressure jacket positioned within the syringe support structure in accordance with the device of the present disclosure;

FIG. 14 is a portion of the pressure jacket and syringe support structure of FIG. 13 enlarged for magnification purposes;

FIG. 15 is a perspective view of a snap ring provided for securing the pressure jacket to an injector housing of the injector head in accordance with the device of the present disclosure;

FIG. 16 is a side plan view of the snap ring of FIG. 15;

FIG. 17 is a cross-sectional view of the snap ring of FIG. 15 taken along line 17-17;

FIG. 19 is an assembled perspective view of a portion of the syringe of FIG. 18;

FIG. 20 is an assembled top plan view of a portion of the syringe of FIG. 18;

FIG. 21 is a perspective view of the syringe of FIG. 18 with a plunger member and a connector removed therefrom;

FIG. 22 is a perspective view of an alternative embodiment of the syringe in accordance with the device of the present disclosure in which the coupling members of the plunger member are positioned parallel to an alignment flange on the syringe body;

FIG. 23 is a cross-sectional view taken along line 23-23 in FIG. 21;

FIG. 24 is a cross-sectional view taken along line 24-24 in FIG. 21;

FIG. 25 is a perspective view of the connector of the syringe of FIG. 18 coupled to a tubing set in accordance with the device of the present disclosure;

FIG. 26 is a right-side perspective view of the injector head of the fluid delivery system in accordance with another embodiment of the device of the present disclosure;

FIG. 27 is an exploded perspective view of a syringe support structure illustrating a splash shield in accordance with the device of the present disclosure;

FIG. 28 is an assembled perspective view of the syringe support structure of FIG. 27;

FIG. 37 is a side plan view of the knuckle and the injector head in the inject position;

FIG. 38 is a side plan view of the knuckle and the injector head in the fill position;

FIG. 39 is a side plan view of the knuckle and the injector head in the level position;

FIG. 40 illustrates the ranges of a tilt angle for the injector head in accordance with the device of the present disclosure;

DESCRIPTION OF THE PREFERRED EMBODIMENTS

Figure 1A:
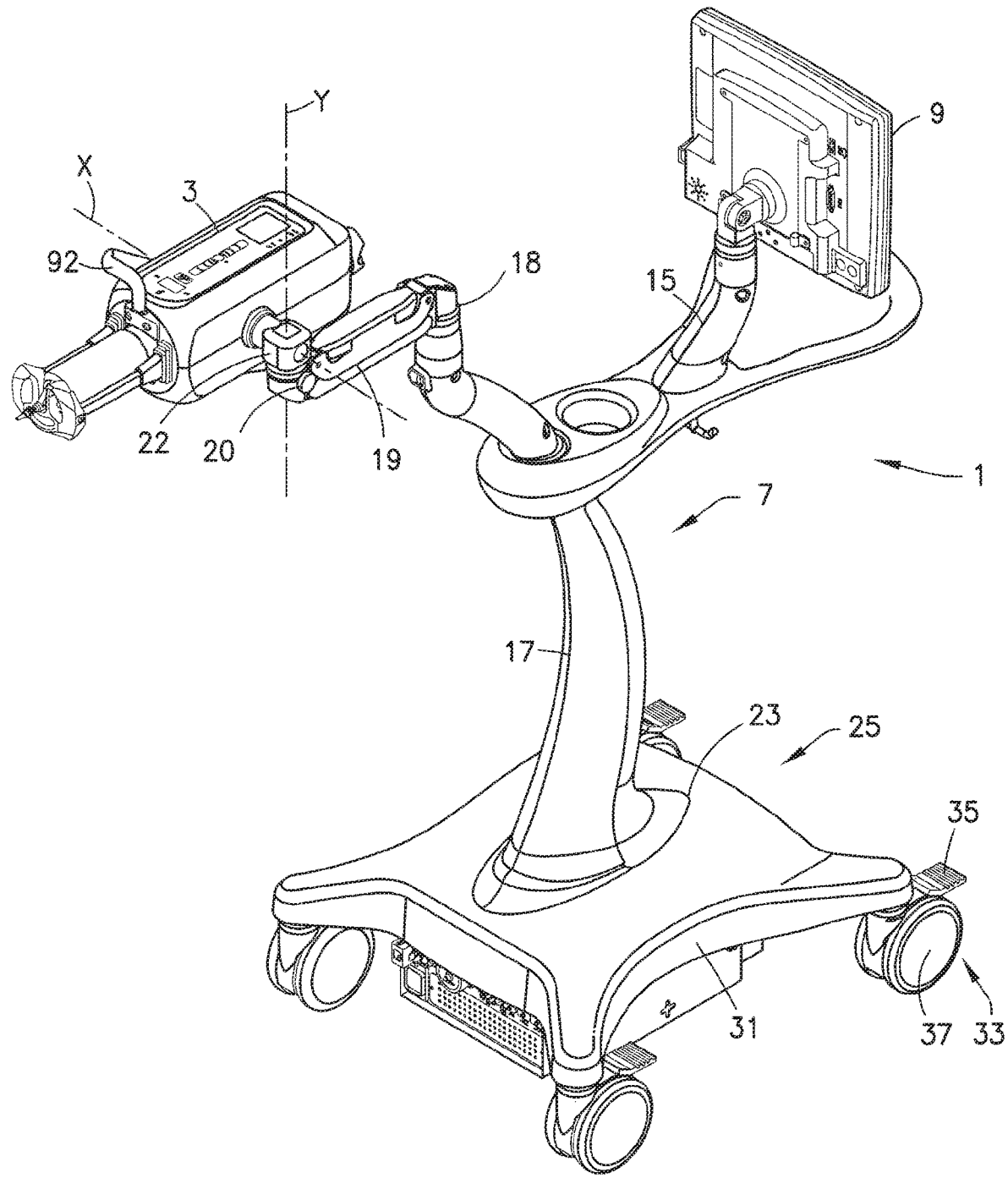
FIG. 1A is a perspective view of a fluid injection system in accordance with the device of the present disclosure.

For purposes of the description hereinafter, the terms "upper", "lower", "right", "left", "vertical", "horizontal", "top", "bottom", "lateral", "longitudinal", and derivatives thereof, shall relate to the device of the present disclosure as it is oriented in the drawing figures. However, it is to be understood that the device of the present disclosure may assume various alternative variations, except where expressly specified to the contrary. It is also to be understood that the specific devices illustrated in the attached drawings, and described in the following specification, are simply exemplary embodiments of the device of the present disclosure. Hence, specific dimensions and other physical characteristics related to the embodiments disclosed herein are not to be considered as limiting.

The injector disclosed herein is related to the injector disclosed in U.S. Pat. Nos. 7,326,189; 7,334,639; 7,549,977; 7,556,619; 7,563,249; and 7,611,503 and U.S. Patent Application Publication No. 2008/0086087, which are hereby incorporated by reference in their entirety.

Figure 2:
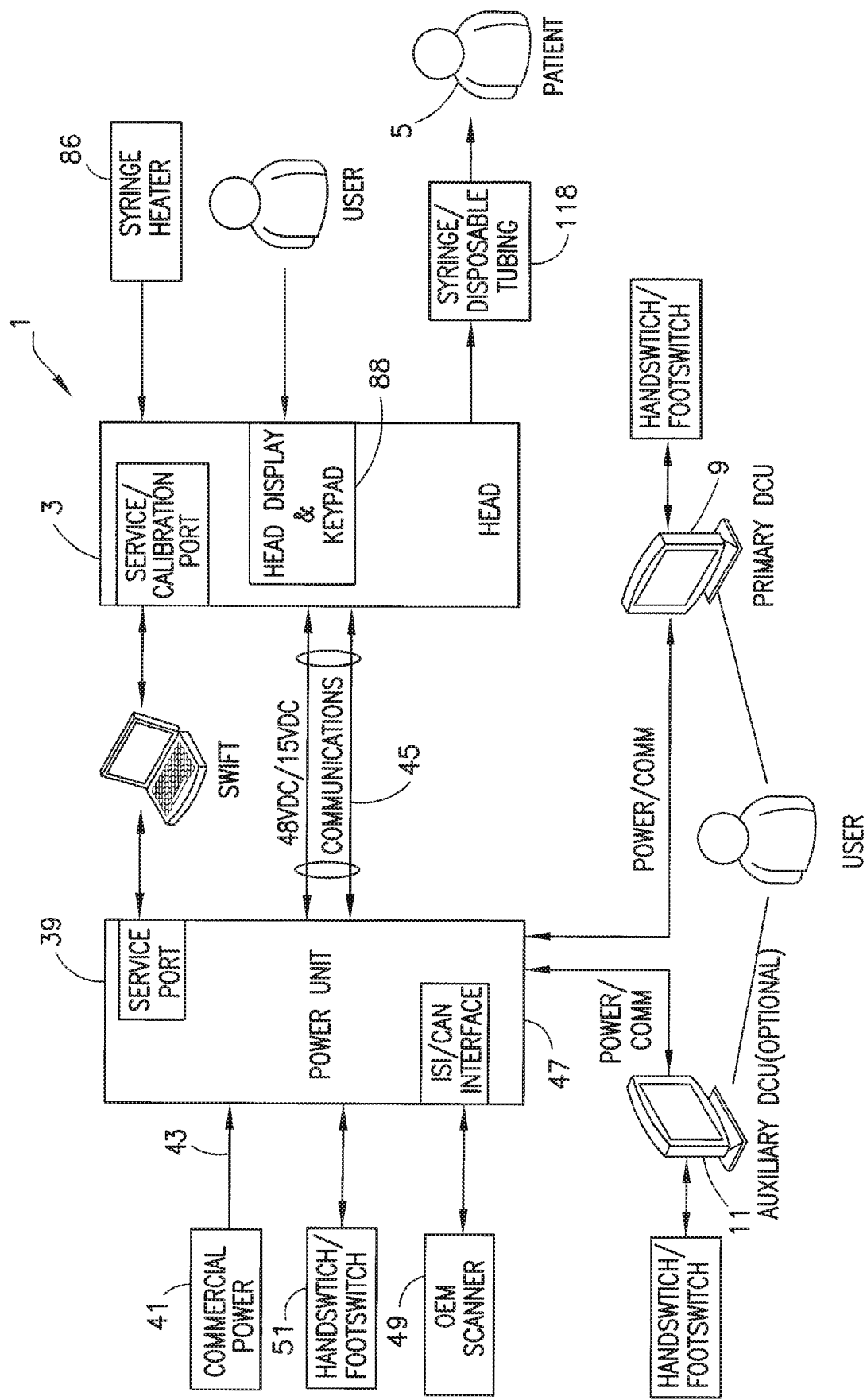
FIG. 2 is a schematic block diagram of the fluid injection system of FIG. 1A.

With reference to FIGS. 1A and 2, a fluid injection system, generally denoted as reference numeral 1, includes an injector head 3 for delivering a fluid to a patient 5; a mounting structure 7 pivotally connected to the injector head 3 and configured to support the injector head 3; and a control system, including a display control unit (DCU) 9, operationally coupled to the injector head 3 for controlling an injection procedure. The DCU 9 includes a color liquid crystal display (LCD) screen with a touch screen overlay that is interfaced to an internal computer board. The DCU 9 is responsible for providing a graphical user interface (GUI) to the user and allows information to be input via the touch screen to the control system.

In addition, the injection system 1 can support multiple display DCUs, such as auxiliary DCU 11 shown in FIG. 2. When multiple DCUs are incorporated into the injection system 1, the multiple DCUs are not operated in a master/slave configuration. Instead, a user may interface with any of multiple input devices such as the display controls (discussed hereinafter) of the injector head 3 or any of the multiple DCUs 9, 11. While the user is interacting with one of these input devices, control inputs from the others are ignored (i.e., locked). However, their display outputs can be updated by the active input device. When the user has returned to the Home screen of a DCU, the lock on all input devices is removed. Another way in which control may be given up and the lock removed, is through the use of timeouts. If the interface device is not interacted with by the user for a period of time (5 seconds for injector head inputs, 30 seconds for DCU inputs), an audible or visual indicator is asserted and control is given up by the active input device.

Figure 1B:
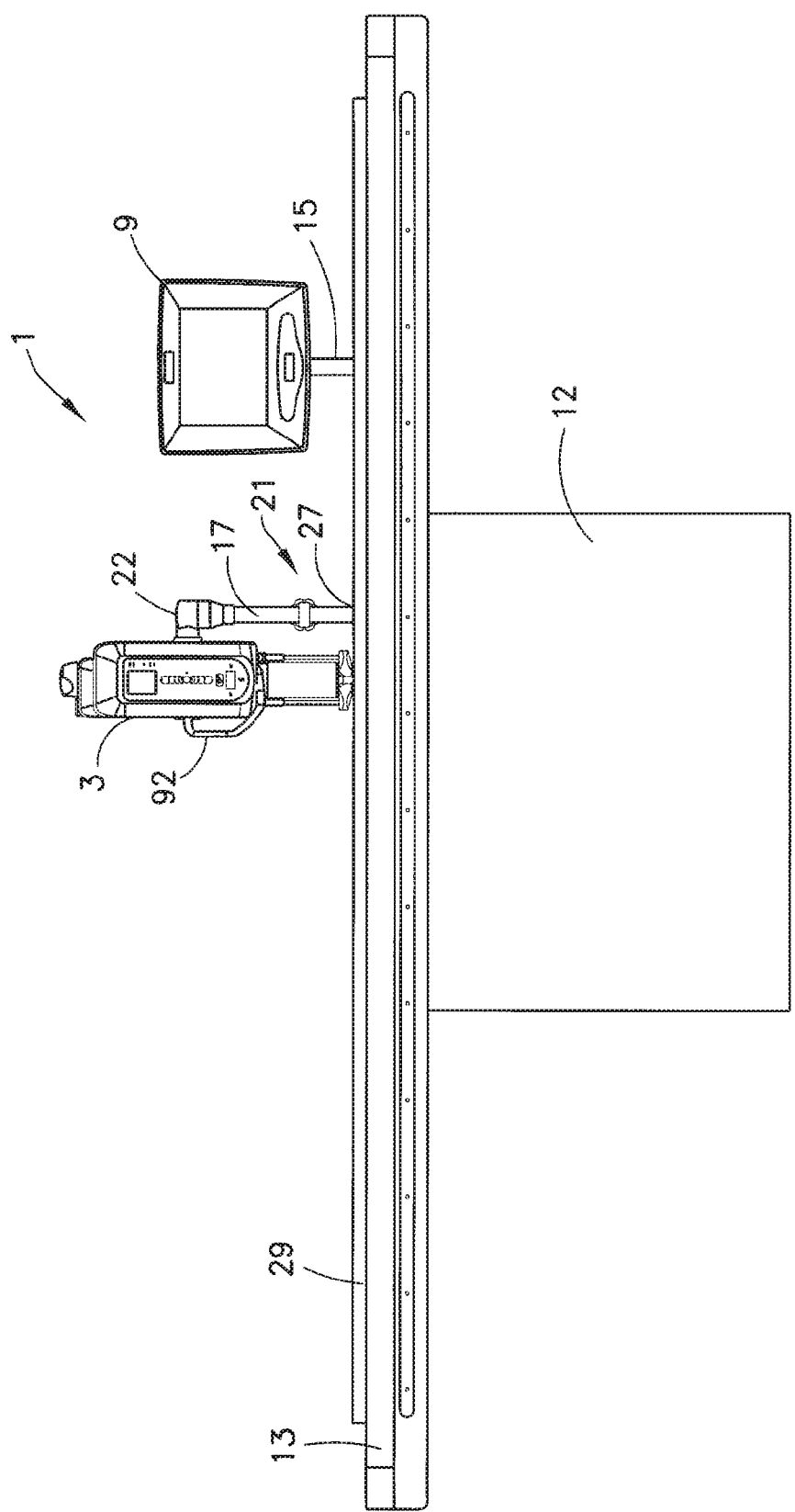
FIG. 1B is a perspective view of the fluid injection system of FIG. 1A mounted to the rail of an examination table.

FIG. 1A illustrates the injection system 1 provided as a mobile unit and FIG. 1B illustrates the injection system 1 as being mounted to an examination table 13. In each configuration, the mounting structure 7 of the fluid injection system 1 includes a first support arm 15 extending from a support column 17 for supporting the DCU 9. A second support arm 19 extends from the support column 17 and generally supports the injector head 3. The second support arm 19 has a first end 18 pivotally coupled to the support column 17 and a second end 20 pivotally coupled to a knuckle 22 of the injector head 3.

In the configuration shown in FIG. 1B, the support column 17 is associated with a rail interface 21 which is generally adapted to attach the fluid injection system 1 to a hospital bed or an examination table 13 supported by a stand 12. Alternatively, and as shown in FIG. 1A, the support column 17 may include a pedestal interface 23 for attaching the fluid injection system 1 to a movable pedestal 25. The fluid injection system 1 may be configured to be attached to the examination table 13 or the movable pedestal 25 to provide the maximum amount of flexibility and ease in utilizing the fluid injection system 1. Thus, when the fluid injection system 1 is mounted to the examination table 13, a rail mount 27 is attached to a rail 29 of the examination table 13. This allows the rail interface 21 to be removably attached to the rail mount 27. Thus, the rail mount 27 indirectly supports the DCU 9 and the injector head 3. In an alternative embodiment, only the injector head 3 is indirectly supported by the rail mount 27, and an additional rail mount is utilized to independently support the DCU 9 at a different location on the rail 29 of the examination table 13.

Referring to FIG. 1A, the movable pedestal 25 provides mobility to the fluid injection system 1 and height adjustability features. The movable pedestal 25 includes a base 31 for holding loose components related to the fluid injection system 1 and the power cables associated therewith. The base 31 may also include a power socket (not shown) that interfaces with the power cables (not shown) within the base 31. Thus, a single external power cable (not shown) may be plugged directly into the power socket (not shown) to provide sufficient power for operation of the entire fluid injection system 1. The movable pedestal 25 may also include a plurality of casters 33 having lockable brakes 35 and wheels 37. It is to be understood that the aforementioned configurations are for exemplary purposes only and are not to be considered as limiting the placement and positioning of the fluid injection system 1.

With reference to FIG. 2, the fluid injection system 1 also includes a power supply unit 39 operationally coupled to the injector head 3, the DCU 9, and the optional auxiliary DCU 11. The power supply unit 39 houses power conversion devices (not shown) for converting domestic and international standardized commercial AC line voltages 41 into internal +15 and +48V DC power for the fluid injection system 1. The power supply unit 39 is coupled to the commercial AC line voltages 41 by a plug 43. In addition, the power supply unit 39 houses an Ethernet switch card (not shown). The switch card serves as the communications hub for the entire system. Ethernet communications data 45 is passed to the switch card and routed to the appropriate recipients. An Imaging Systems Interface (ISI) module 47 is also housed in the power supply unit 39. The ISI module 47 allows the fluid injection system 1 to connect to a common commercial X-Ray scanner 49.

The fluid injection system 1 may further include a hand or foot switch 51 provided to initiate an injection. The hand/foot switch 51 can be connected to either the DCU (primary 9 or auxiliary 11) or the power supply unit 39. If a foot switch is utilized, it is designed to be placed on the floor for foot activation.

Figure 3:
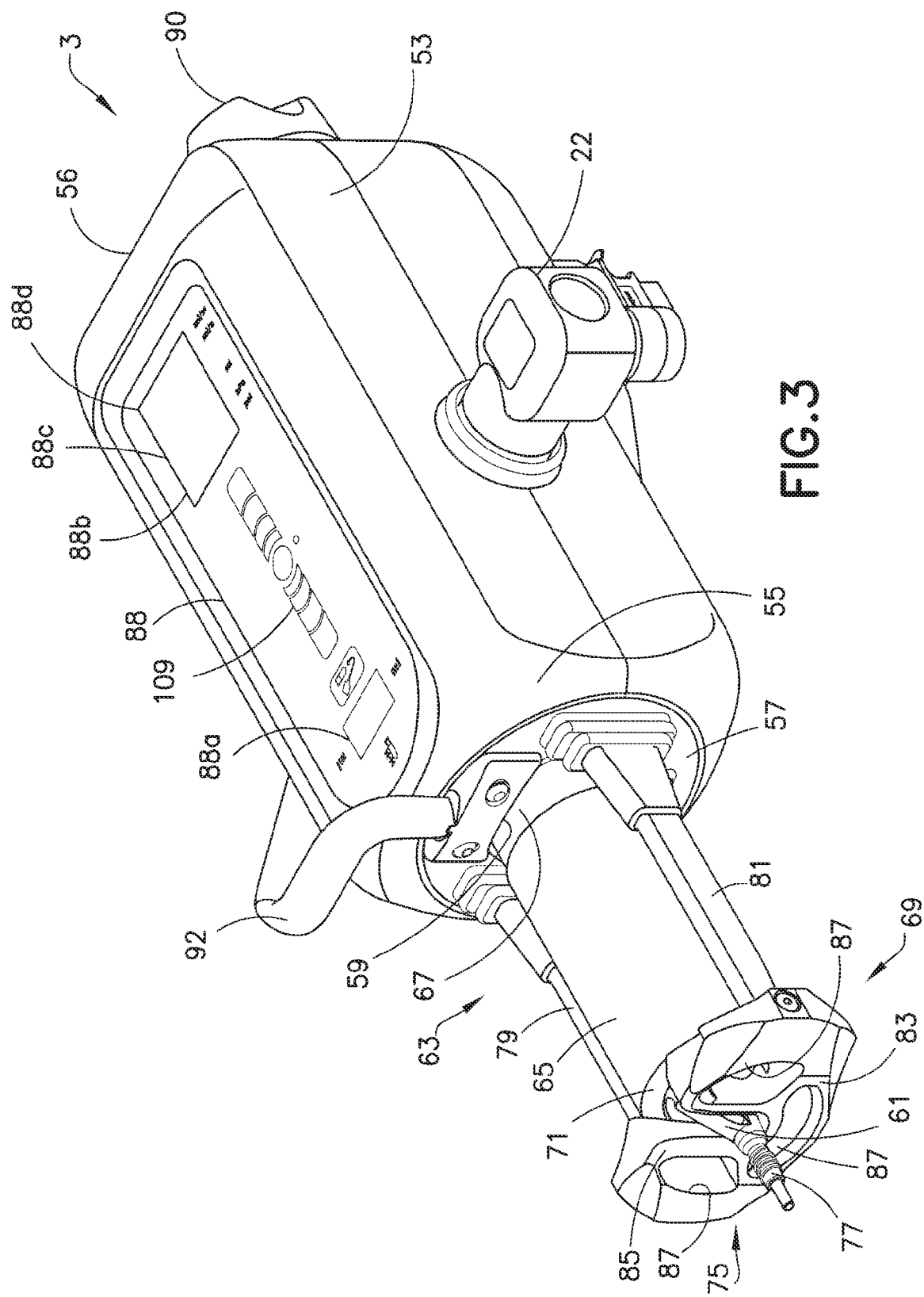
FIG. 3 is a right-side perspective view of an injector head of the fluid injection system of FIG. 1A.
Figure 4:
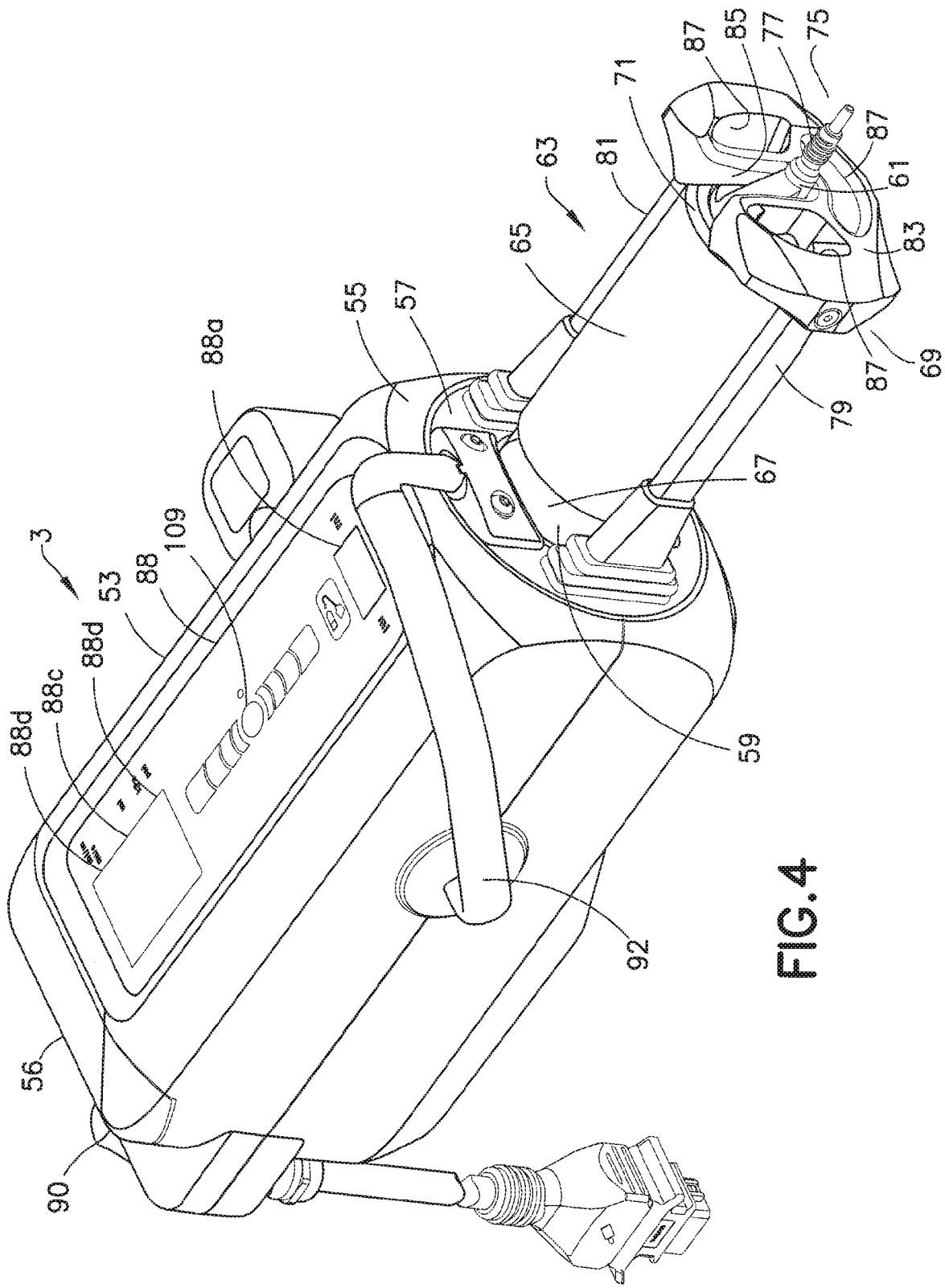
FIG. 4 is a left-side perspective view of the injector head of FIG. 3.

With reference to FIGS. 3 and 4 and with continued reference to FIGS. 1A and 2, injector head 3 includes an injector housing 53 having a front end 55 and a back end 56. A faceplate 57 is attached to the front end 55 of the injector housing 53 and encloses the front end 55 of the injector housing 53. The faceplate 57 may be secured to the front end 55 of the injector housing 53 by conventional means (i.e., mechanical fasteners and the like) or be integrally formed with the injector housing 53.

The injector housing 53 has a central opening 59 aligned with a central passage defined by the faceplate 57, and through which an injector drive piston of the injector head 3 is extendable and retractable. The details of the injector head 3 and, more particularly, the injector drive piston are described in U.S. Pat. No. 5,383,858, which is incorporated by reference herein in its entirety. As described further herein, the injector head 3 is generally used to actuate a syringe 61 used in a fluid injection procedure, such as an angiographic procedure.

With reference to FIGS. 5-8 and with continued reference to FIGS. 3 and 4, a pressure jacket assembly, generally denoted as reference numeral 63, is associated with the injector head 3. The pressure jacket assembly 63 supports the syringe 61 and mounts the syringe 61 to the injector head 3. Generally, the pressure jacket assembly 63 extends outward from the front end 55 of the injector housing 53 and is used to support the syringe 61 during the fluid injection procedure. The pressure jacket assembly 63 is generally comprised of the faceplate 57, discussed previously, a cylindrical pressure jacket 65 having a coupling end 67 for connecting the pressure jacket 65 to the faceplate 57, and a syringe support structure 69 for supporting the syringe 61. The faceplate 57 may be considered to be a part of the injector housing 53, as well as form part of the pressure jacket assembly 63.

Figure 9:
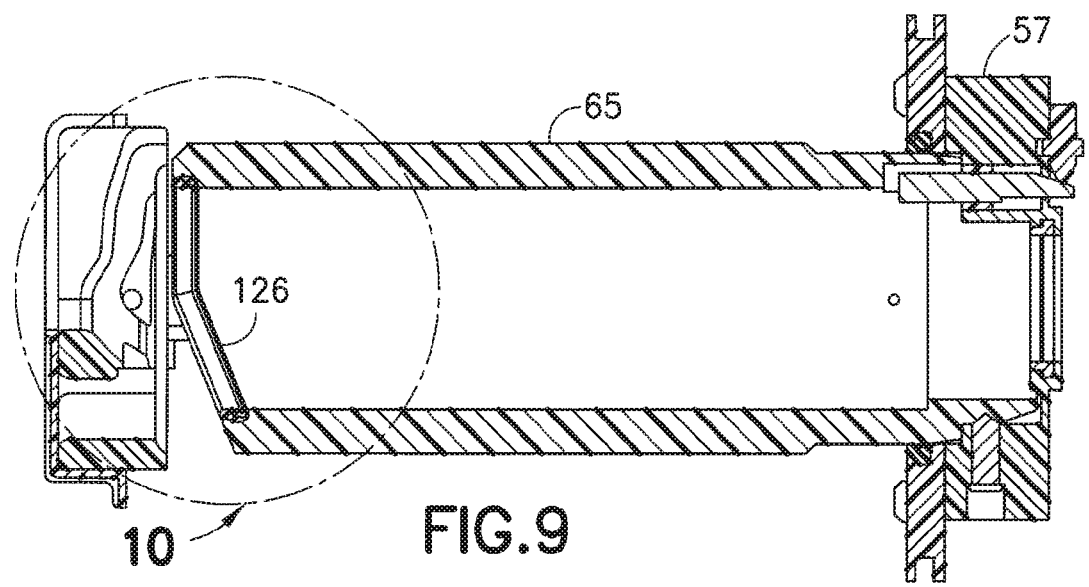
FIG. 9 is a cross-sectional view of the pressure jacket positioned within the syringe support structure in accordance with the device of the present disclosure.
Figure 10:
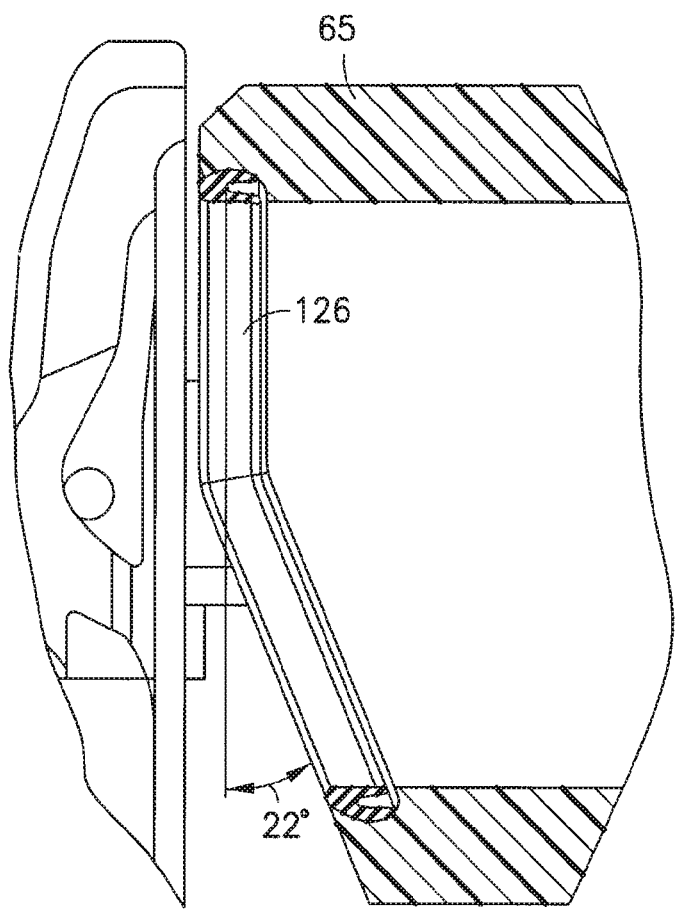
FIG. 10 is a portion of the pressure jacket and syringe support structure of FIG. 9 enlarged for magnification purposes.

The pressure jacket 65 is a generally cylindrical structure having a front or distal end 71 and the rear coupling end 67. The distal end 71 of the pressure jacket 65 defines a syringe receiving mouth or opening 122 for receiving the syringe 61 into the pressure jacket 65. An outer edge of the distal end 71 of the pressure jacket 65 includes a grooved interface 124 configured to receive a wiper seal 126. The wiper seal 126 is positioned within the grooved interface 124 of the pressure jacket 65 as shown in FIGS. 5 and 6. The purpose of the wiper seal 126 is to reduce the amount of contrast passing into the small gap (not shown) between the pressure jacket 65 and the syringe 61 when the syringe 61 is loaded into and/or unloaded from the pressure jacket 65. When contrast gets onto the inside wall of the pressure jacket 65, it makes it difficult to insert the syringe 61 and it is detrimental to visibility of the contents of the syringe 61. The gap between the pressure jacket 65 and the syringe 61 is necessary to accommodate the tolerances associated with each part. During high pressure injection procedures, the syringe 61 swells up and contacts the inside of the pressure jacket 65 thus gaining additional support from the pressure jacket 65. The wiper seal 126 includes a generally ring-shaped body 128 that is designed to be flexible in nature to accommodate the manufacturing variation in the syringe 61 as well as the swelling that occurs during high pressure injections. The ring-shaped body 128 of the wiper seal 126 is designed to follow the outer edge at the opening 122 of the pressure jacket 65. It is custom molded to follow the exact 22 degree bevel contained on the pressure jacket 65 (see FIGS. 9 and 10) and is tapered to help the user align and insert the syringe 61 into the pressure jacket 65.

The coupling end 67 of the pressure jacket 65 faces the faceplate 57 and is configured to be connected to the faceplate 57. The coupling end 67 of the pressure jacket 65 is designed such that it allows the pressure jacket 65 to be installed by simply pushing it axially into the central opening 59 of the faceplate 57 of the injector head 3. The coupling end 67 of the pressure jacket 65 includes a locating slot 130, a ramped surface 132, and a groove 134. The locating slot 130 is provided to allow a user to properly align the pressure jacket 65 with the faceplate 57 by aligning the locating slot 130 with a notch 136 provided in the central opening 59 of the faceplate 57 as shown in FIG. 12. With reference to FIGS. 11-17 and with continued reference to FIGS. 5-8, the ramped surface 132 and groove 134 are designed to interact with a snap ring 138 provided in the central opening 59 of the faceplate 57 in order to secure the pressure jacket 65 to the faceplate 57. The snap ring 138 includes a generally ring-shaped body member 140 having a locating slot 142 provided in an upper portion thereof. The locating slot 142 is configured to be aligned with the notch 136 of the central opening 59 of the faceplate 57 when the snap ring 138 is positioned within the central opening 59 as shown in FIG. 12.

As the pressure jacket 65 is pushed into the central opening 59, the snap ring 138 located within the central opening 59 rides up over the ramped surface 132 of the coupling end 67 of the pressure jacket 65 and drops into the groove 134. The snap ring 138 provides sufficient inward radial force to hold the pressure jacket 65 in the desired position. Upon removal, the snap ring 138 again rides up over the ramped surface 132 of the coupling end 67 of the pressure jacket 65 and completely disengages from the pressure jacket 65. This bayonet design has two distinct advantages. First, the user can install and remove the pressure jacket 65 without the use of tools or excessive force. This is beneficial because it allows the user to easily remove the pressure jacket 65 for cleaning and then reinstall it. Secondly, it allows the pressure jacket 65 to move axially during a high pressure injection. This is important because during a high pressure injection, the entire syringe interface stretches forward due to the extreme forces. The syringe 61 swells up inside the pressure jacket 65 contacting the inside wall of the pressure jacket 65. Due to the friction between the syringe 61 and the pressure jacket 65, the pressure jacket 65 is pulled forward along with the syringe 61. If the interface between the pressure jacket 65 and the injector head 3 does not permit this axial motion during high pressure injections, relative motion between the syringe 61 and pressure jacket 65 occurs. This relative motion causes an undesirable stick-slip phenomenon between the syringe 61 and the pressure jacket 65.

The pressure jacket 65 has an inner diameter sized to smoothly but snugly receive the outer diameter of the syringe 61. The pressure jacket 65 is desirably made of a material capable of restraining the outward expansion of the syringe 61 during an injection procedure. The syringe 61 by itself is typically not capable of withstanding the high pressures associated with certain fluid injection procedures, such as angiography. The syringe 61 may be made of a relatively inexpensive medical grade plastic material and may be disposable (i.e., single use). Alternatively, the syringe 61 may be a multi-patient use syringe. Typical plastics for the syringe 61 include polypropylene, polyethylene, and polycarbonate. The pressure jacket 65 is desirably reusable and made of a material capable of withstanding pressures up to about 1200 psi and higher. For example, the pressure jacket 65 may be made of metal, such as steel or aluminum. However, as explained further hereinafter, it is advantageous for the syringe 61 to be visible through the pressure jacket 65 so that an operator of the fluid injection system 1 may view the syringe 61 during an injection procedure. Accordingly, the pressure jacket 65 is preferably made of a substantially clear plastic material, such as polycarbonate, for viewing the syringe 61 during an injection procedure.

An alternate to the use of an integrally formed coupling end 67 at the end of the pressure jacket 65 for connecting the pressure jacket assembly 63 to the injector head 3, a separate coupling member (not shown) may be utilized. The coupling member may be used in place of the coupling end 67 and is cylindrically shaped in a similar manner to the pressure jacket 65. The coupling member has a front or distal end configured for connection to the pressure jacket 65 and a rear or proximal end configured for connection to the faceplate 57. The coupling member may be made of any of the materials discussed previously in connection with the pressure jacket 65.

With specific reference to FIGS. 18-25, the syringe 61 used in the fluid injector system 1 generally includes an elongated, cylindrical syringe body 74 having a front or distal end 75 and a rear or proximal end 76. The syringe body 74 has an injection section 78 formed at the distal end 75. As discussed further hereinafter, the syringe body 74 includes an expansion section 150 at the proximal end 76. A generally cylindrical center section or main body 152 of the syringe body 74 connects the injection section 78 and the expansion section 150. The main body 152 has a relatively uniform outer diameter. The injection section 78 tapers to form an elongated injection neck 77, which has a relatively small inner diameter compared to the inner diameter of the main body 152. The injection section 78, injection neck 77 generally forms the discharge outlet of the syringe 61. The syringe support structure 69 is configured to support the injection section 78 of the syringe 61. The injection neck 77 includes a distal end structure, which is adapted to connect via a suitable luer fitting to tubing, for example, connected to a catheter used in an angiographic procedure, as discussed in greater detail hereinafter. A suitable luer fitting for this purpose is disclosed in published PCT Application No. PCT/US99/18892 (WO 00/10629), entitled "Connector And Tubing Assembly For Use With A Syringe", the disclosure of which is incorporated herein by reference in its entirety. More desirably, the distal end structure will include a connector as discussed in greater detail hereinafter.

Additional features of the syringe 61 will now be discussed with continuing reference to FIGS. 19-26. The injection section 78 of the syringe body 74 generally tapers inward toward a central axis L of the syringe body 74. The injection section 78 includes a conical portion 154 tapering from the cylindrical shaped center section or main body 152 to the injection neck 77. The conical portion 154 defines an alignment flange or tab member 156. This alignment flange or tab member 156, in one embodiment, defines a hollow space or area therein. The alignment flange or tab member 156 is provided as a means to view the fluid within the syringe 61. Additionally, the alignment flange or tab member 156 acts as a visual indicator for properly aligning the syringe 61 in the pressure jacket 65. Further, the alignment flange or tab member 156 provides a convenient handle for manipulating the syringe 61 and inserting it into the pressure jacket 65. Secondarily, the hollow space defined by the alignment flange 156 may operate as an air bubble trap. Desirably, the alignment flange or tab member 156 generally extends the distance between the main body 152 of the syringe body 74 and the injection neck 77.

Figure 18:
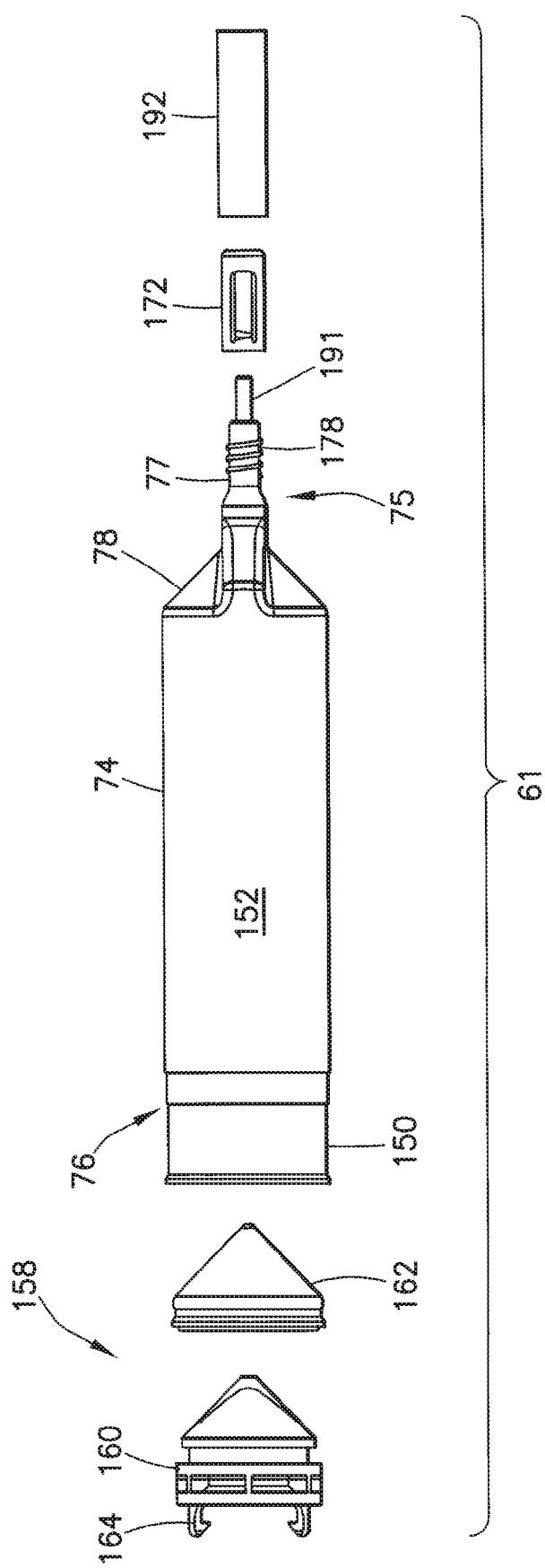
FIG. 18 is a top plan exploded view of a syringe for use with the fluid injection system in accordance with the device of the present disclosure.

A plunger member 158 is slidably supported within the syringe body 74. The plunger member 158 may include a plunger core 160 that is molded from a hard polymeric material, for example, polycarbonate material. A seal or plunger cover 162 is also attached to the plunger core 160. The plunger member 158 is configured for connection to an injector drive piston (not shown) for imparting motive forces thereto. The plunger core 160 includes a coupling end 164 that faces the proximal end 76 of the syringe body 74 and is configured to engage the injector drive piston. The coupling end 164 includes a pair of flexible lug or coupling members 227 that extend outward from the coupling end 164 for engaging the injector drive piston. The coupling members 227 each have an engagement arm 228. The coupling members 227 define a slot 230 therebetween. The slot 230 is configured to receive an injector end plate attached to the injector drive piston. As mentioned hereinabove, the alignment flange or tab member 156 provides a last resort air containment feature when the distal end of the plunger member 158 extends into and "bottoms-out" in the conical portion 154. Any unnoticed air bubbles will tend to collect in the hollow area defined by the alignment flange or tab member 156 during operation of the injector head 3. As shown in FIG. 18, the coupling members of the coupling end 164 of the plunger member 158 of the syringe 61 are positioned perpendicularly to the alignment flange or tab member 156. This syringe is configured for use with the injector head illustrated in FIGS. 3 and 4. Alternatively, the coupling members 227 of the coupling end 164 of the plunger member 158 of the syringe 61' may be positioned parallel to the alignment flange or tab member 156 as shown in FIG. 22. This type of syringe is configured for use with the injector head of FIG. 26.

With specific reference to FIGS. 23 and 24, prior art syringes for medical injection procedures are often stored with a pre-positioned syringe plunger. A difficulty with current disposable plastic syringes is that these syringes exhibit plastic creep over time and especially during sterilization heat cycles. This causes the plastic syringe to swell, particularly in a plunger area about the syringe plunger. This often makes it difficult to load prior art plastic syringes in front loading pressure jackets because of swelling in the plunger area where the syringe plunger is stored.

The syringe 61 of the device of the present disclosure stores the plunger member 158 in the expansion section 150 to accommodate the expansion and plastic creep of the plastic syringe body 74 as discussed hereinafter. The expansion section 150 is desirably formed adjacent the cylindrical center section or main body 152 of the syringe body 74 and at the proximal end 76 of the syringe body 74. However, the expansion section 150 may be formed or located at any position in the syringe body 74 wherein the plunger member 158 is to be stored. At the expansion section 150, a wall 166 of the syringe body 74 narrows from a thickness T to a reduced wall thickness $T_r$. Thus, an inner diameter $ID_{es}$ of the expansion section 150 is larger than an inner diameter $ID_{cs}$ of the cylindrical center section or main body 152. The reduced wall thickness $T_r$ at the expansion section 150 allows the expansion section 150 to expand outward under the force exerted by the plunger member 158 without an outer diameter $OD_{es}$ of the expansion section 150 becoming larger than an outer diameter $OD_{es}$ of the center section 152 of the syringe body 74. Both an outer surface 168 of the wall 166 of the syringe body 74 and an inner surface 170 of the wall 166 of the syringe body 74 taper or are stepped to form the reduced wall thickness $T_r$ at the expansion section 150. In particular, the outer surface 168 of the wall 166 of the syringe body 74 is tapered or stepped inward toward the central axis L of the syringe body 74 and the inner surface 170 of the wall 166 of the syringe body 74 tapers or is stepped outward away from the central axis L of the syringe body 74 to form the reduced wall thickness $T_r$. An alternative configuration to the foregoing is to only taper or step the inner surface 170 of the wall 166 of the syringe body 74 outward away from the central axis L of the syringe body 74. Another alternative is to only taper or step the outer surface 168.

The reduced wall thickness $T_r$ at the expansion section 150 of the syringe 61 accommodates the expansion and plastic creep of the plastic syringe body 74 even after long periods of storage. Thus, even after such long storage periods, the syringe 61 with pre-positioned plunger member 158 may be quickly and easily inserted into front-loading pressure jacket systems, such as pressure jacket assembly 63. As stated previously, the plunger member 158 is stored in the expansion section 150. When the syringe 61 is inserted into the pressure jacket 65 and ready for use, the plunger member 158 is engaged by the injector drive piston in the manner discussed previously and moved forward from the expansion section 150 to the center section or main body 152 of the syringe 61, which may be referred to as the "working zone" of the syringe 61.

With reference to FIGS. 18-20 and 25, the syringe 61 further includes a connector 172 for coupling a patient tubing set 174 having a connecting portion 175 to the syringe 61. The connector 172 is configured to be positioned over the injection neck 77 of the syringe 61. The connector 172 includes a threaded portion 176 that cooperates with a threaded portion 178 on the syringe 61. The connector 172 includes a cooperating slot 180 into which a flange 182 of the tubing set 174 slides to align an inner passage (not shown) of the tubing set 174 with an opening (not shown) in the connector 172. The flange 182 cooperates with a retaining member or flange 184 formed upon a forward end of the connector 172 and a forward abutment wall 186 on the connector 172 (which form the slot 180 therebetween) to substantially prevent relative axial movement/separation of the connector 172 and the tubing set 174 after connection thereof.

The retaining member 184 is desirably of a generally circular shape with an opening 188 therein. The opening 188 allows passage of a generally cylindrical portion 190 of the tubing set 174 therethrough when the connector 172 and the tubing set 174 are connected. The width of the opening 188 is desirably somewhat smaller than the diameter of the generally cylindrical portion 190, such that the connecting portion 175 of the tubing set 174 snaps into place when aligned with the connector 172 and sufficient force is applied in the direction of arrow F. Alternatively, there may be a clearance provided between flange 182 and retaining member 184. The connector 172 is desirably fabricated from a resilient polymeric material, such as polycarbonate. In addition, the connecting portion 175 is desirably fabricated from a host of other resilient polymeric materials and the tubing set 174 is desirably fabricated from flexible polymeric materials of either single wall, coextruded, or braided designs.

After the tubing set 174 is connected to the connector 172, the connector 172 is rotated relative to the injection neck 77 of the syringe 61, such that a tapered end 191 of the injection neck 77 passes through the opening (not shown) in the connector 172 to mate with a correspondingly tapered interior wall (not shown) on the rearward portion of the tubing set 174 to form a fluid tight connection. Because the opening 188 is smaller than the cylindrical portion 190 of the tubing set 174, the retaining member 184 prevents disconnection of the connector 172 and the connecting portion 175 of the tubing set 174 after a fluid tight connection has been made. The connector 172 and the tubing set 174 are configured to remain in a connected state under all circumstances and forces normally experienced before and during connection of the tubing set 174 to the syringe 61. Prior to use, a dust cover 192 may be provided over the connector 172 and injection neck 77 to protect the contents of the syringe 61 from contamination.

Further details of the connector 172 are described in U.S. Patent Application Publication No. 2005/0171487, which is hereby incorporated by reference in its entirety.

With reference to FIGS. 3 and 4, the syringe support structure 69 is provided for the purpose of constraining the syringe 61 during pressurized injections. One embodiment of the syringe support structure 69, as shown in FIGS. 3 and 4, includes at least one, and desirably two, support arms 79, 81 extending outward from the injector housing 53. The support arms 79, 81 are configured to pivot up and down with respect to the injector housing 53. The support arms 79, 81 have rear or proximal ends extending into the injector housing 53, and distal ends projecting outward from the injector housing 53. The distal ends of the support arms 79, 81 are interconnected by a syringe retaining wall or member 83. The syringe retaining member 83 may be affixed to the support arms 79, 81 by conventional mechanical fasteners (i.e., bolts) and the like. The syringe retaining member 83 defines a central syringe receiving slot 85 that is substantially vertically oriented and is configured to receive and support the injection neck 77 of the injection section of the syringe 61. The syringe retaining member 83 further defines one or more openings 87, which are spaced radially outward from the syringe receiving slot 85. The syringe receiving slot 85 and openings 87 permit the operator of the fluid injection system 1 to view the syringe 61 during an injection procedure.

The support arms 79, 81 are generally configured to be movable between a first position, wherein the syringe retaining member 83 receives the injection neck 77 and cooperates with the injection section of the syringe 61 and prevents removal of the syringe 61 from the pressure jacket 65, and a second rotated position wherein the injection neck 77 and the injection section of the syringe 61 are disengaged sufficiently from the syringe receiving slot 85 and syringe retaining member 83 to allow removal of the syringe 61 from the pressure jacket 65. In particular, in the second position, the injection neck 77 is disengaged sufficiently from the syringe receiving slot 85 and the injection section is sufficiently decoupled from the syringe retaining member 83 to allow the syringe 61 to be removed easily from the front loading pressure jacket 65. Desirably, in the second position, the support arms 79, 81 and syringe retaining member 83 are spaced a distance below the pressure jacket 65 and syringe 61. With the support arms 79, 81 in the first position, the syringe support structure 69 is in a syringe-engaged position. When the support arms 79, 81 are moved to the second position, the syringe support structure 69 is generally in a syringe-disengaged or removal position or configuration. A removable heating element 86 (see FIG. 2) may be attached to the pressure jacket 65 to keep the fluid provided in syringe 61 pre-heated at 37° C.

An alternative embodiment of an injector head 3' having an alternative syringe support structure 69' as illustrated in FIG. 26 allows the pivoting of syringe support structure 69' sideways or rotated approximately 90 degrees from the previous embodiment shown in FIGS. 3 and 4. More specifically, the syringe support structure 69' includes at least one, and desirably two, support arms 79', 81' extending outward from a faceplate 57' of an injector housing 53'. The support arms 79', 81' are configured to pivot right and left with respect to the injector housing 53'. The support arms 79', 81' have rear or proximal ends extending into the injector housing 53', and distal ends projecting outward from the injector housing 53'. The distal ends of the support arms 79', 81' are interconnected by a syringe retaining wall or member 83'. The syringe retaining member 83' may be affixed to the support arms 79', 81' by conventional mechanical fasteners (i.e., bolts) and the like.

In this alternative embodiment, the pivoting axis of the syringe support structure 69' is largely vertical in nature as opposed to the previous embodiment where the pivoting axis is largely horizontal in nature. This second embodiment has the distinct advantage of neutralizing the effects of gravity associated with the previous embodiment. The structural components that make up the syringe support structure 69' may contain substantial mass and therefore may be heavily influenced by the effects of gravity. This can lead to a drooping effect causing the syringe support structure 69' mechanism to fall away from its intended closed position. The second embodiment combats this by ensuring the pivoting action is largely perpendicular to the vector of gravitational pull.

Another distinct advantage of the second embodiment is the ability to assist with manipulating the injector head 3'. An essential component of normal use of the injector head 3' is the ability to rotate it from the largely upward fill/purge position to a largely downward injection position. This rotation is a common air management technique whereas the air is purged out of the syringe 61 in the upward position and then rotated downward for the procedure. This is done to ensure any un-expelled air remains trapped in the back of the syringe 61 and is not injected into the patient. Users often grasp the back of the injector head 3' with their left hand and the front of the injector head 3' with their right hand to accomplish this rotating action. Grasping and pushing on the syringe support structure 69' can potentially open the syringe support structure 69' because the rotation axis of the injector head 3' is normal to the same plane as the rotation axis of the syringe support structure 69'. The second embodiment eliminates this tendency to open when pushed by ensuring the syringe support structure 69' pivots via an axis that is largely perpendicular to axis of rotation of the injector head 3'.

Yet another advantage of the second embodiment is superior resistance to contrast fouling. The syringe support structure 69' is comprised of many components with a large number of crevices for contrast to get trapped in. Orienting the syringe support structure 69' such that it pivots sideways prevents contrast from building up in some of the more problematic areas.

With reference to FIGS. 27 and 28, a splash shield 250 may be provided to cover the syringe retaining member 83' of the syringe support structure 69'. During a typical angiography procedure, the user fills the syringe 61 with contrast while the injector head 3' is in the upward position allowing the syringe 61 to point largely towards the ceiling. Once the desired amount of fluid is obtained, the user purges the air out of the syringe 61. With the syringe tip being the highest point, the air naturally rises to the top and escapes the syringe 61. Occasionally, the user spills some contrast onto the syringe support structure 69' during this filling or purging process, which can result in a phenomenon known as contrast fouling. The purpose of the splash shield 250 is to divert any spilled contrast away from the syringe support structure 69' and into a more desirable location. One of the benefits of the splash shield 250 is that it snaps onto the syringe retaining member 83' of the syringe support structure 69' in a very simple manner. It is held in place by very specific geometry and cantilever beam undercut fingers 252. This allows the user to remove the splash shield 250 for cleaning or replacement. Another benefit is that it can be manufactured from a clear polymeric material. This allows the user to maintain visibility of the syringe 61. It also allows light to pass through, maintaining a high level of syringe visibility. Increased visibility is important to the user because they must verify that no air is trapped in the syringe 61 prior to injection. The splash shield 250 may also be provided to cover the syringe retaining member 83 of the syringe support structure 69 of the first embodiment discussed hereinabove.

Figure 43:
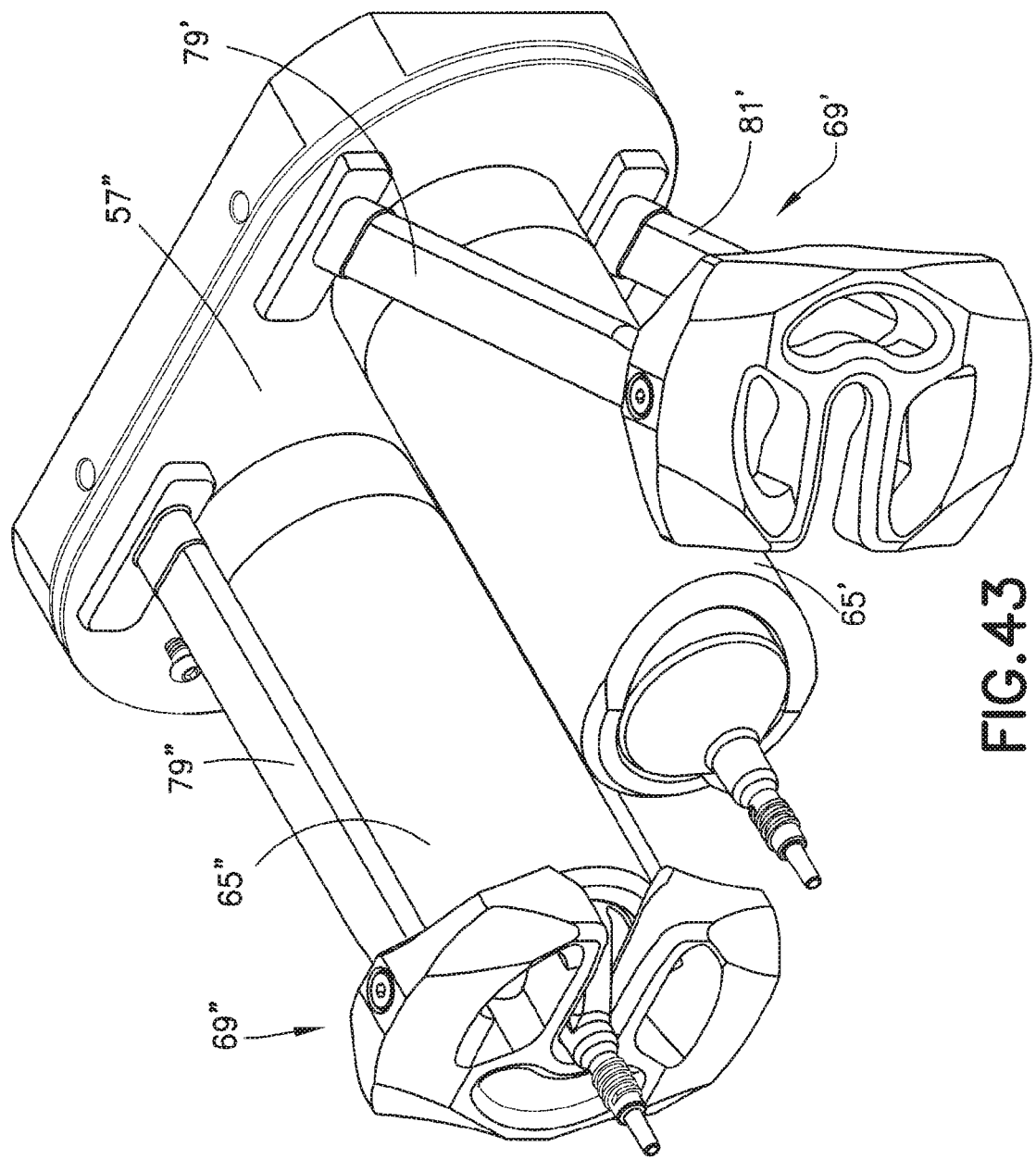
FIG. 43 is a right-side perspective view of a portion of the injector head of the fluid delivery system in accordance with another embodiment of the device of the present disclosure.
Figure 44:
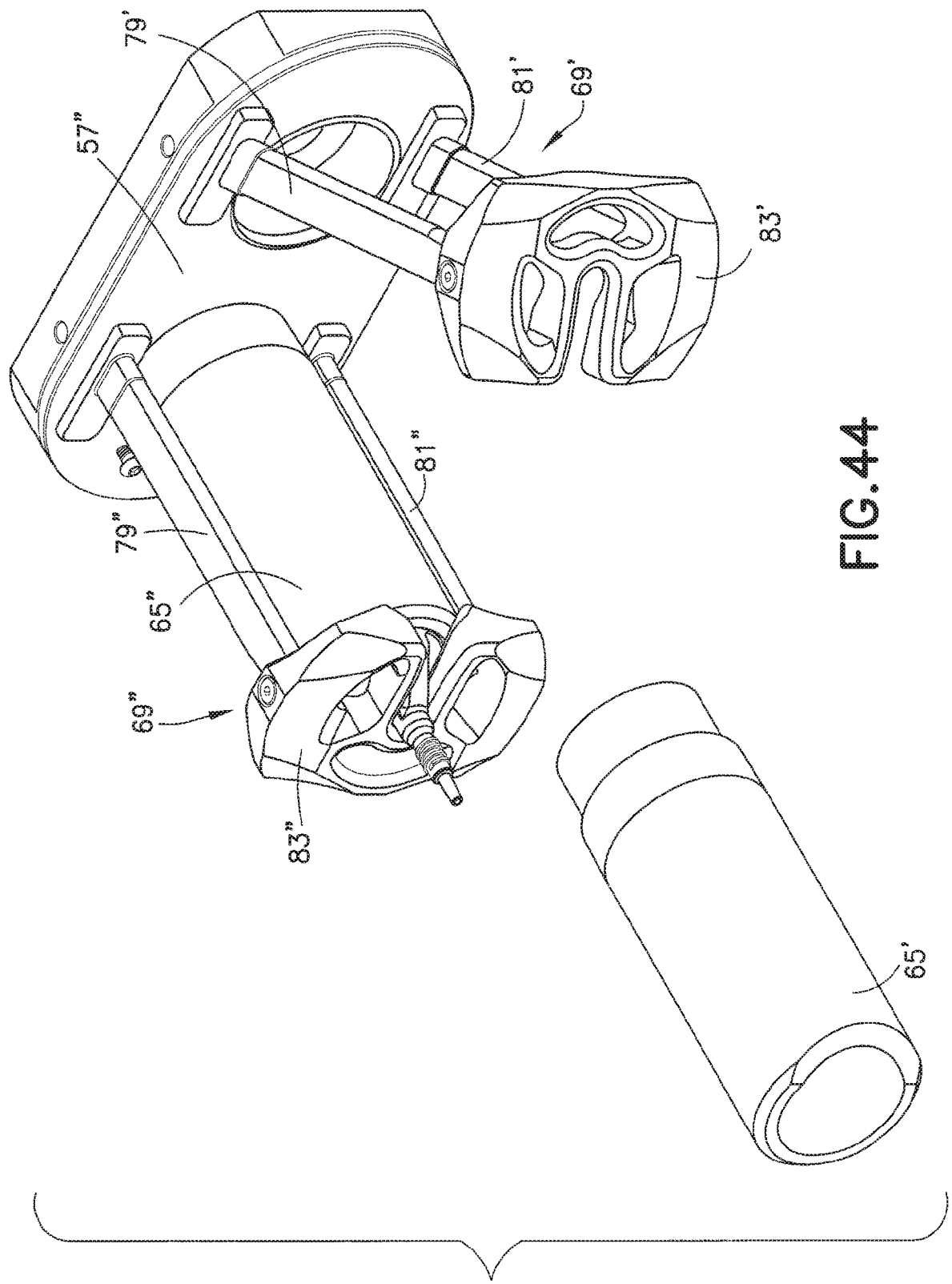
FIG. 44 is a front right side exploded perspective view of the portion of the injector head of the fluid delivery system of FIG. 43.
Figure 45:
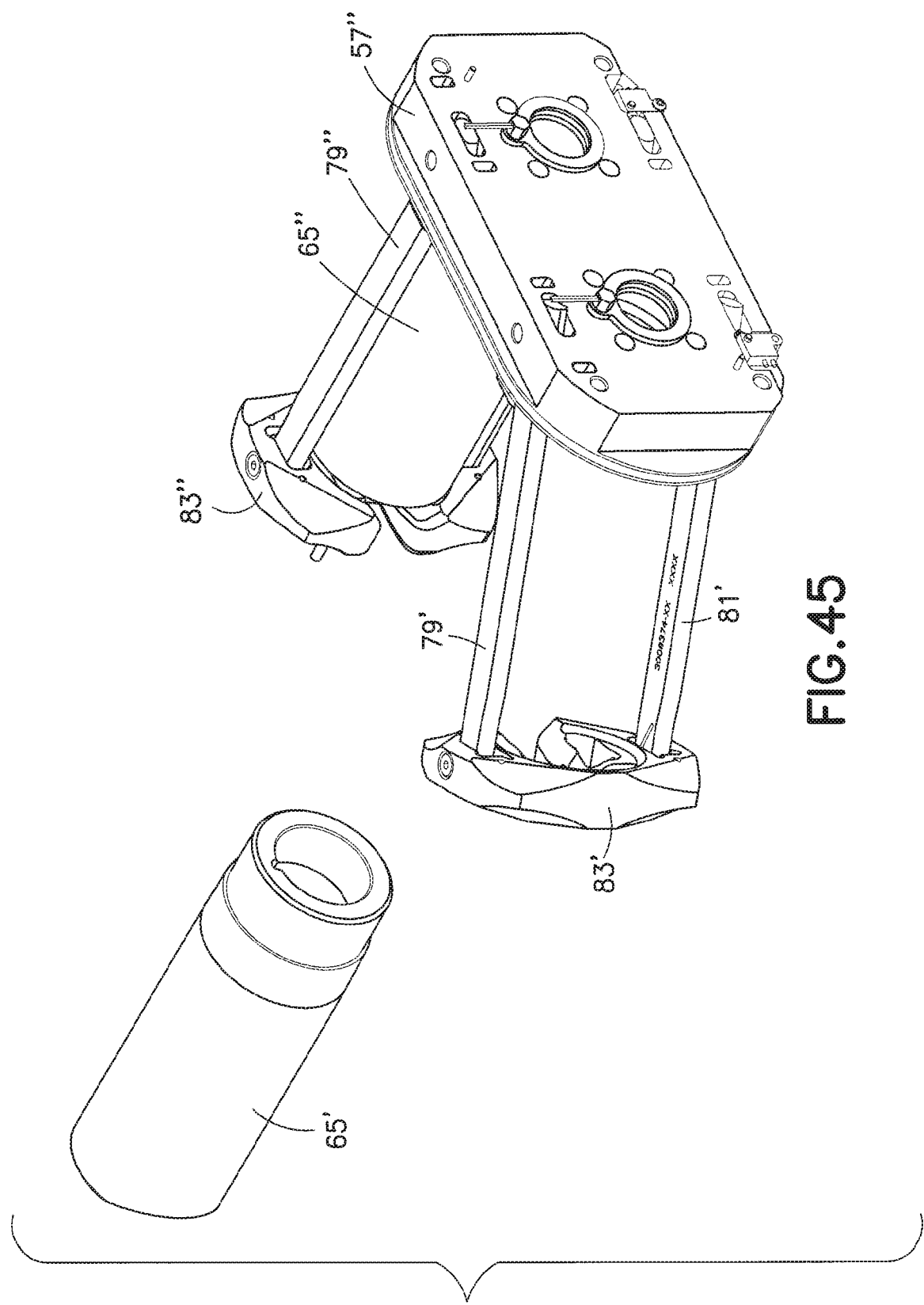
FIG. 45 is a rear right side exploded perspective view of the portion of the injector head of the fluid delivery system of FIG. 43.
Figure 46:
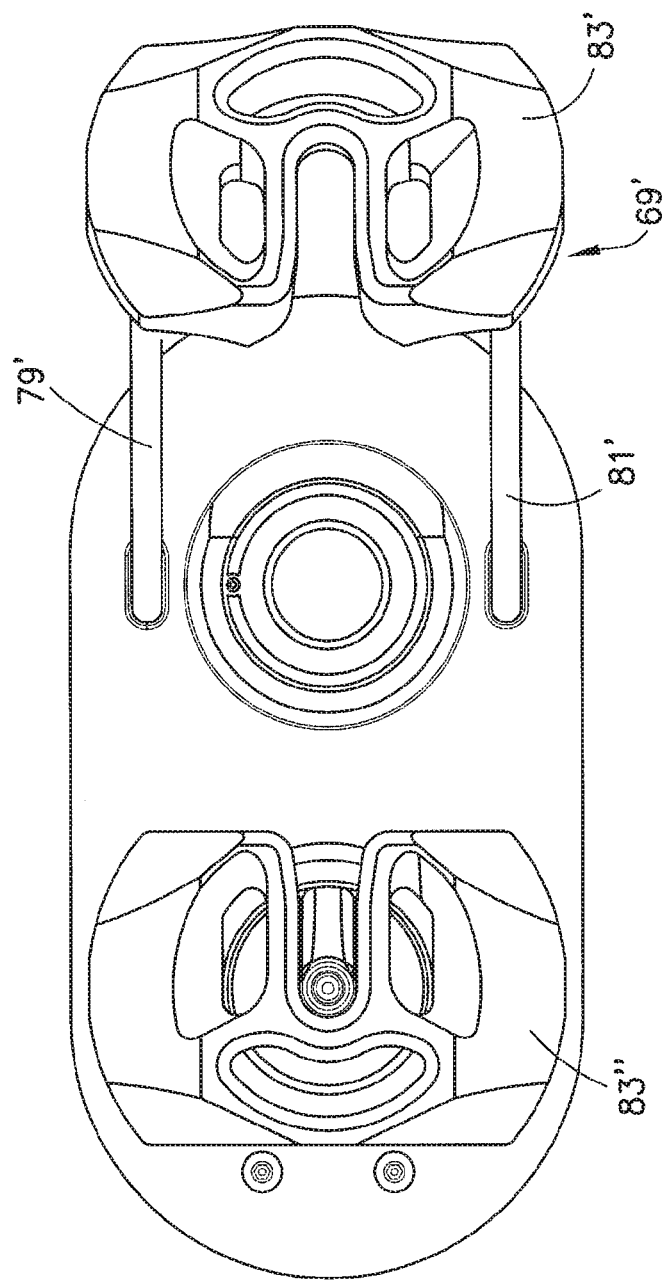
FIG. 46 is a front plan view of a portion of the injector head of the fluid delivery system of FIG. 43 with one of the pressure jacket assemblies removed therefrom.

With reference to FIGS. 43-45, this alternative embodiment of the syringe support structure 69' may be incorporated into a dual syringe injector head having a first syringe support structure 69' capable of supporting a first pressure jacket 65' and syringe and a second syringe support structure 69" capable of supporting a second pressure jacket 65" and syringe. The first syringe support structure 69' includes at least one, and desirably two, support arms 79', 81' extending outward from a faceplate 57" of the injector housing. The support arms 79', 81' are configured to pivot right and left with respect to the injector housing. The support arms 79', 81' have rear or proximal ends extending into the injector housing, and distal ends projecting outward from the injector housing. The distal ends of the support arms 79', 81' are interconnected by a syringe retaining wall or member 83'. The second syringe support structure 69" also includes at least one, and desirably two, support arms 79", 81" extending outward from the faceplate 57" of the injector housing. The support arms 79", 81" are configured to pivot right and left with respect to the injector housing. The support arms 79", 81" have rear or proximal ends extending into the injector housing, and distal ends projecting outward from the injector housing. The distal ends of the support arms 79", 81" are interconnected by a syringe retaining wall or member 83".

Such a dual syringe injector head allows for various modes of operation as discussed in greater detail in U.S. Pat. Nos. 8,133,203 and 7,553,294, which are hereby incorporated by reference in their entirety. More specifically, the following modes of operation may be utilized by the dual syringe injector: a mode for sequential injection from the syringes, a mode for simultaneous injection from the syringes into a single injection site and a mode for simultaneous injection from the syringes into different injection sites.

In the case of a sequential injection, a fluid can be injected from only one of the syringes at a time. For example, the syringe associated with pressure jacket 65' can contain contrast medium, while the syringe associated with pressure jacket 65" can contain a flushing fluid such as saline, which can be sequentially injected into a patient using a variety of protocols as known in the art.

During simultaneous injection into a single site, the syringe associated with pressure jacket 65' can, for example, be loaded or filled with contrast medium, while the syringe associated with pressure jacket 65" can, for example, be loaded with a diluent or flushing fluid such as saline. In this mode, contrast medium or other fluid in the syringe associated with pressure jacket 65' can, for example, be diluted or mixed with fluid in the syringe associated with pressure jacket 65" to a desired concentration by simultaneous injection from the syringe associated with pressure jacket 65' and the syringe associated with pressure jacket 65" as programmed by the operator.

In the case of a simultaneous injection to different injection sites, the syringe associated with pressure jacket 65' and the syringe associated with pressure jacket 65" can, for example both be filled with the same injection fluid (for example, contrast medium). Injection of the contrast medium at two different sites, as opposed to a single site, can, for example, enable delivery of a desired amount of contrast medium to a region of interest at a lower flow rate and a lower pressure at each site than possible with injection into a single site. The lower flow rates and pressures enabled by simultaneous injection into multiple sites can, for example, reduce the risk of vascular damage and extravasation.

With continuing reference to FIGS. 2-4, the injector housing 53 includes a piston (not shown) positioned therein for connecting and actuating the plunger member 158 of the syringe 61. An actuation system (not shown) is also positioned within the injector housing 53 for moving the piston. The actuation system may include a gear train and linear ball screw; a brushless DC motor coupled to the gear train and linear ball screw; and a motor amplifier operationally coupled to the motor as is known in the art. A controller (not shown) internal to the injector housing 53, controls piston movement via the brushless DC motor. Syringe filling and injections of contrast agents are controlled by this controller. The controller communicates with the operator via the graphical user interface of the DCU 9. The injector housing 53 also includes a display 88 for displaying information regarding the activities and state of operation of the injector head 3. The display 88 is positioned on a top portion of the injector housing 53 and displays information regarding volume remaining, programmed flow rate, programmed pressure, and programmed volume. Each of these items may be presented to the operator on the display by an independent light emitting diode (LED) display. For instance, volume remaining may be displayed on LED display 88a, pressure may be displayed on LED display 88b, programmed volume may be displayed on LED display 88c, and flow rate may be displayed on LED display 88d (see FIG. 3). The injector housing 53 further includes a knob 90 positioned at a back end 56 thereof. The knob 90 is an external manual device directly coupled to the injector head actuation system. The knob 90 allows the user to move the piston manually in either the forward or reverse direction. Accordingly, the purpose of the knob 90 is to allow an operator to: (1) manually purge air out of the syringe 61; and (2) retract (or extend) the syringe plunger in the event of a system power failure so as to allow for installation or removal of the syringe 61. A handle 92 is also positioned on injector housing 53 for repositioning or transporting the fluid injection system 1.

Figure 29:
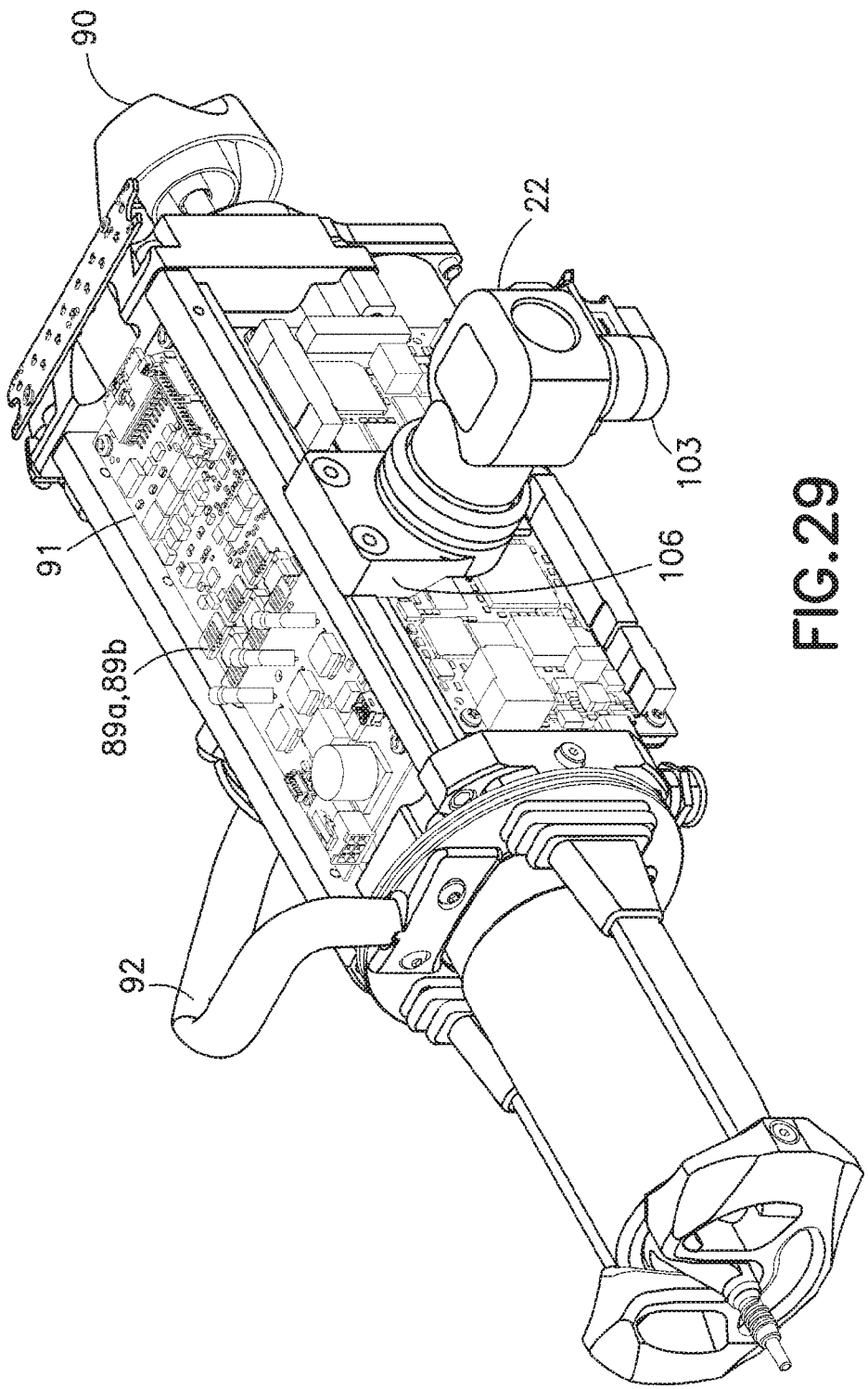
FIG. 29 is a right-side perspective view of the injector head of FIG. 3 with the injector housing removed.
Figure 30:
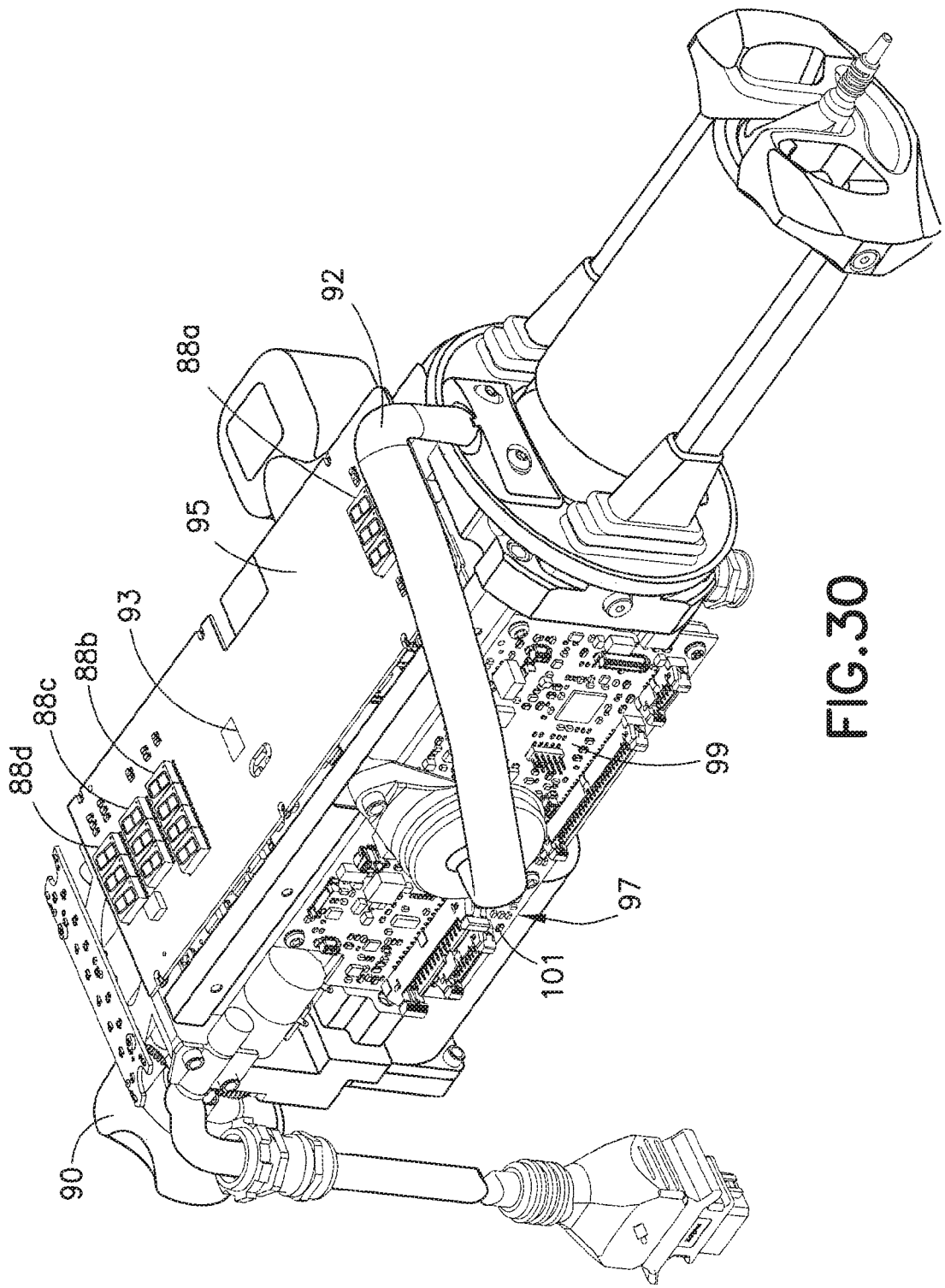
FIG. 30 is a left-side perspective view of the injector head of FIG. 4 with the injector housing removed.

With reference to FIGS. 29 and 30 and continued reference to FIGS. 3 and 4, various sensors are also provided within the injector housing 53. For instance, the fluid injector system 1 employs a method of thermal management that prevents the system from being damaged due to thermal overload of the electronics and motor drive. Accordingly, four (4) thermal sensors are used within the injector housing 53 to measure the temperature at strategic locations. Two temperature sensors 89a, 89b are mounted on a motor drive printed circuit board (PCB) 91. These temperature sensors 89a, 89b measure the temperature of power transistors below heat sinks on the motor drive PCB 91. Another temperature sensor 93 is mounted on the underside of a head display PCB 95, which is mounted directly over the motor drive PCB 91. The purpose of this temperature sensor 93 is to measure the heat plume generated above the heat sinks of the power transistors. A final temperature sensor 97 is mounted on a signal management PCB 99. The purpose of this temperature sensor 97 is to measure the injector housing ambient temperature. Those of skill in the art will appreciate that the placement and linking together of multiple temperature sensors can vary while achieving the same result.

The four sensors 89a, 89b, 93, 97 are interfaced to analog to digital converters and are read by the controller mounted within the injector housing 53. Software provided on the controller continuously monitors the temperature signal provided by each sensor 89a, 89b, 93, 97. The software is programmed with predefined limits for which it will inhibit motor amplifier operation if these limits are exceeded. The primary source of heat during a high pressure injection procedure is due to the high amounts of power delivered to the motor via the motor amplifier. During the design of fluid injection system 1, each of the electrical components is derated to produce the derated component value. This derating process is as follows. The performance parameters of a component (e.g., maximum power dissipation, maximum voltage, etc.) are specified by manufacturers. To improve reliability of a product and decrease probability of device or component failure, engineers typically apply derating criteria during the design so that components will never operate at the maximum ratings. For example, a resistor may have a maximum power dissipation of 0.5 Watts. If this value is derated by 50%, then the maximum power it will ever dissipate is 0.25 Watts. Such derating drastically improves product reliability. The predefined limits discussed above are based on derated component values, so that if an injection is started and the temperature exceeds the predefined limit, there is substantial headroom to allow the injection to complete, without exceeding the absolute maximum working temperature of the weakest component in the fluid injection system 1. Any suitable temperature sensor may be used for this purpose. Desirably, the temperature sensors 89a, 89b, 93, 97 are 1.5V, SC70, Multi-Gain Analog Temperature Sensors with Class-AB Output (Part No. LM94022/LM94022Q) manufactured by National Semiconductor Corporation.

In addition and as discussed hereinabove, the fluid injection system 1 may be provided in one of two different configurations: a mobile pedestal, as shown in FIG. 1A; and a fixed examination table-rail configuration that allows the operator to attach both the injector head 3 and the DCU 9 to the rail of the examination table, as shown in FIG. 1B.

Many examination table and bed manufacturers offer beds that have lift, pan, and tilt functionality, allowing the physician to position the patient three-dimensionally in a surgical suite. Accordingly, a three-axis accelerometer 101 is provided on signal management PCB 99 to allow the fluid injection system 1 to establish a reference plane with respect to the room floor surface. The output signal of the accelerometer 101 is read by the controller provided in the injector housing 53 to first determine if there is an offset in the coordinate system of the accelerometer 101 and in which axis of the Cartesian system this offset exists. If the offset is detrimental to air management, then the operator is alerted via a message provided on the graphical user interface of DCU 9 to reposition the injector head 3 or the entire fluid injection system 1 to a normal surface parallel to the floor.

The three-axis accelerometer 101 is a Micro-Electro-Mechanical System (MEMS) integrated circuit (IC) that is sensitive to accelerative forces with earth gravity being the primary force of interest. Any suitable three-axis accelerometer 101 may be utilized. For instance, the accelerometer 101 may be a three-axis low-g micromachined accelerometer (Part No. MMA7361LC) manufactured by Freescale Semiconductor.

In addition, several other sensors may be provided in the injector head 3 to provide signals to the controller so that it can be determined if the syringe 61 has been loaded, if the syringe retaining wall 83 has been properly positioned, if the plunger has been sufficiently advanced, and/or the angle of tilt of the injector head 3. The determination of the tilt angle of the injector head 3 will be discussed in greater detail hereinafter.

With reference to FIGS. 31-40 and continued reference to FIGS. 3 and 4, as discussed hereinabove, the knuckle 22 pivotally supports the injector head 3 on the second support arm 19, thereby allowing the injector head 3 to rotate around the axis labeled X in FIG. 1A. The knuckle 22 includes an L-shaped body portion 102 having a pivot post 103 and a hollow coupling post 104 positioned perpendicularly to the pivot post 103. The pivot post 103 is pivotally connected to the second end 20 of the second support arm 19, thereby allowing the injector head 3 to rotate around the axis labeled Y in FIG. 1A. A connection post 105 is provided having a first end that extends into the coupling post 104 and a second end that is coupled to a bracket 106. The bracket 106 is coupled to the injector head 3 within the injector housing 53, as shown in FIG. 29. This configuration allows the injector head 3 to rotate around the axis labeled X in FIG. 1A while being supported by the connection post 105.

Figure 32:
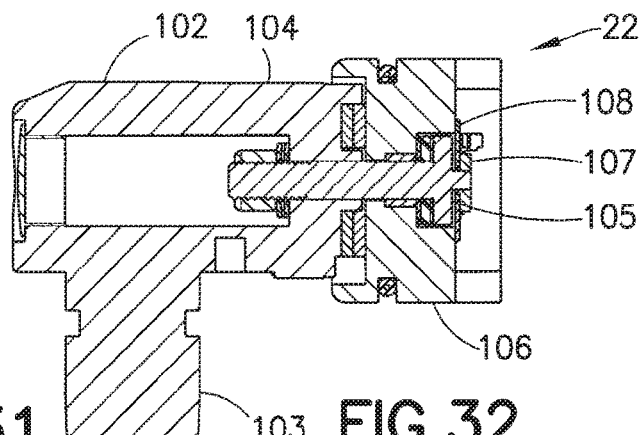
FIG. 32 is a cross-sectional view of the knuckle taken along line 32-32 in FIG. 31.
Figure 34:
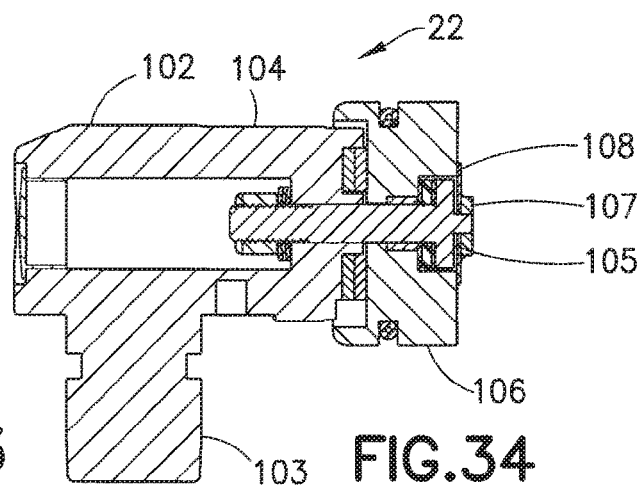
FIG. 34 is a cross-sectional view of the knuckle taken along line 34-34 in FIG. 33.
Figure 35:
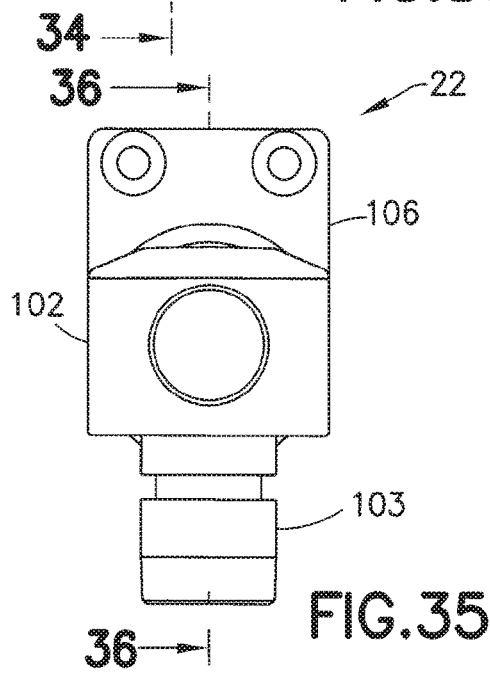
FIG. 35 is a side plan view of a knuckle of a mounting structure for the injector head of FIG. 3 when the injector head is in a level position.
Figure 36:
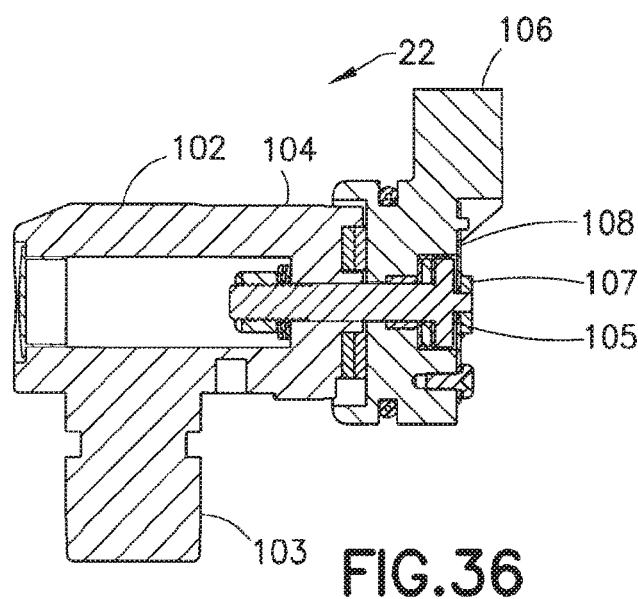
FIG. 36 is a cross-sectional view of the knuckle taken along line 36-36 in FIG. 35.

Current fluid injection systems typically require the use of a sensor that determines the angle of tilt of the head relative to the direction of Earth gravitation using an accelerometer (see, for instance, U.S. Pat. No. 5,868,710). The fluid injection system 1, however, incorporates a device into the knuckle 22 that is used to determine the angular position of the injector head 3 with respect to the support column 17 instead of relative to the direction of Earth gravitation. This device includes a potentiometer 107 that is mounted on a PCB 108 inside the injector head 3 at the location where the injector head 3 interfaces with the knuckle 22. More specifically, and as shown in FIGS. 32, 34, and 36, the PCB 108 and potentiometer 107 are positioned at the second end of the connection post 105.

The potentiometer 107 is a three-terminal electrical device whose center terminal is connected to a wiper mechanism. The other terminals are connected on opposite ends of a resistor surface internal to the potentiometer 107. The wiper mechanism is free to move across the resistive surface. When a voltage is applied across the two outer terminals, the center terminal output is proportional to the position of the wiper. The output of the potentiometer 107 is an angular dependent voltage that is sent to an analog to digital converter (ADC). The signal produced by the ADC is read by the controller provided within the injector housing 53 of the injector head 3. The potentiometer 107 may be any suitable potentiometer based rotary position sensor, such as the 3382-12 mm Rotary Position Sensor manufactured by Bourns or the SMD/Lead Dust-proof Type 12 mm Size SV01 Series Rotary Position Sensor manufactured by Murata. Alternatively, other electrical devices, such as, but not limited to, an encoder or a mechanical or optical switch matrix may be used in place of the potentiometer 107.

Figure 31:
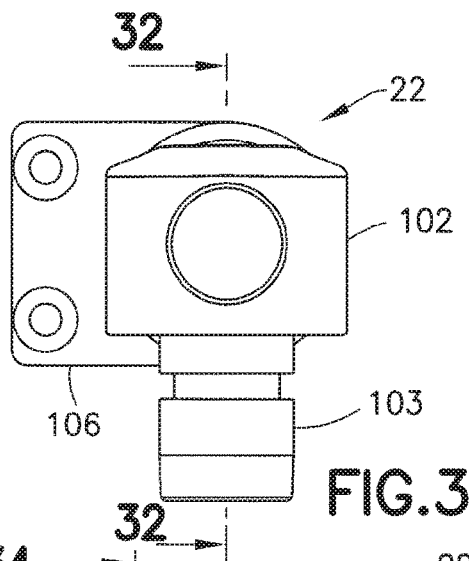
FIG. 31 is a side plan view of a knuckle of a mounting structure for the injector head of FIG. 3 when the injector head is in an inject position.
Figure 33:
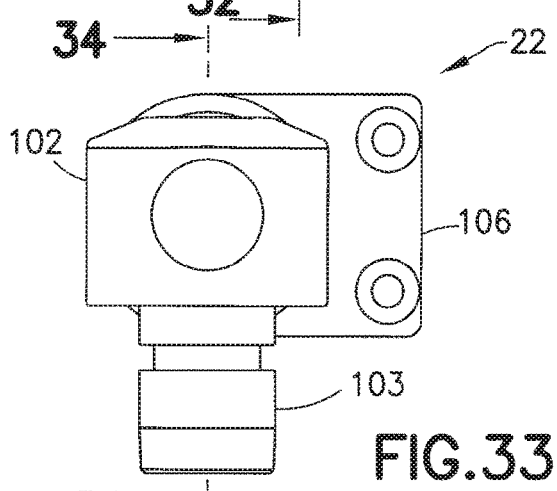
FIG. 33 is a side plan view of a knuckle of a mounting structure for the injector head of FIG. 3 when the injector head is in a fill position.

Accordingly, the potentiometer 107 provided in knuckle 22 is used to provide the controller of the system with an indication of the position of the injector head 3. Head position or tilt sensing is an important safety feature that allows the controller to enforce air management in the syringe 61. When syringe 61 is filled, air within the syringe 61 is displaced by contrast, however, not all of the air is removed. Filling should always be performed with the injector head 3 pointed in a vertical direction as shown in FIG. 38. The orientation of the knuckle 22 during a filling stage is shown in FIGS. 33 and 34. This keeps the residual air at the top of the syringe 61. Once filled, the syringe 61 must be purged of air in the vertical position. In addition, when the syringe 61 is filled and ready for injection, the injector head 3 must be tilted down as shown in FIG. 37. The orientation of the knuckle 22 during an injection stage is shown in FIGS. 31 and 32. The controller, based on a signal received from the potentiometer 107, tracks the position of the injector head 3 at all times. If the injector head 3 is pointed up, the controller will not allow the fluid injection system 1 to arm and inject.

The tilt position signal provided by the potentiometer 107 also controls the head display 88. The operation of the head display 88 can be understood with reference to FIG. 40. Specifically, as noted above, the controller receives a signal from the potentiometer 107 indicative of the angle of the injector head 3 relative to the support column 17. The controller repeatedly samples this signal and determines the angle of the injector head 3 relative to the support column 17. All possible angles of rotation are divided into three regions of operation, illustrated in FIG. 40.

Region 1 is the "purge" region where the angle at which the injector head 3 should be placed for purging the syringe. When the injector head 3 is at an angle within region 1 (from +55° to when the head is pointing straight up at +80°), the injector head 3 will permit hand-operated motion of the plunger drive ram in either the forward or reverse direction, allowing the operator to remove air from the syringe after initial filling, thereby purging the system. This is the only valid purge area where the software will recognize a purge. When the injector head 3 is moved into region 2 (from −10° to +55°, the system can be purged; however, the system does not recognize the purge as valid and will alert the user via the "Smart Sentinel" system discussed hereinafter. In addition, the syringe can also be filled when the injector head 3 is at an angle within region 1, or within region 2. A wide range of movement speeds can be generated, permitting rapid filling of the syringe. While the injector head 3 is in region 1, however, programmed injections are inhibited as described hereinabove. Thus, the operator cannot initiate injection of a subject according to a pre-programmed injection protocol while the injector head 3 is in an upright position. This minimizes the likelihood of accidental injection of air into the subject.

Region 3 is the "inject" region (from −10° to when the head is pointing straight down at −90°). When the injector head 3 is tilted in this region, programmed injections can be initiated. Furthermore, a control button 109 provided on the top of the injector housing 53 (see FIGS. 3 and 4) can be used to move the piston in either the forward or reverse directions; however, the range of movement speeds that can be generated with the control button 109 is substantially narrowed as compared to those available in regions 1 or 2. This permits fine-tuned control of fluid injection (or withdrawal of blood, e.g., to check patency of the catheter) using the control button 109.

The various angular regions noted above, are also associated with display orientations. Specifically, as can be seen in FIG. 40, the display 88 of the injector head 3 includes several independent light emitting diode (LED) displays. For instance, and as described hereinabove, volume remaining may be displayed on LED display 88a, programmed pressure may be displayed on LED display 88b, programmed volume may be displayed on LED display 88c, and programmed flow rate may be displayed on LED display 88d. A volume remaining icon 110 may also be provided on display 88. This volume remaining icon 110 is only illuminated when the injector head 3 is positioned within region 3. The volume remaining icon 110 provides the operator with a quick indication that there is still a volume of a fluid remaining in the syringe if this icon is illuminated, whereas the actual volume remaining in the syringe (e.g., 150 mL) is displayed on the volume remaining LED display 88a. The LED displays are arranged so the noted information can be displayed in either a first (see element 200) or second (see element 300) orientation. When the injector head 3 is in the inject position (down), all of the LED displays are illuminated, as shown by element 300 (i.e., the second orientation). When the injector head 3 is oriented in a Fill/Purge position (up), only the Volume Remaining LED display 88a is illuminated, as shown by element 200 (i.e., the first orientation).

The controller in the injector head 3 drives the various LED displays of the display 88 to produce the display orientation using the LED displays in the manner illustrated by element 200, when the tilt angle is in region 1. Otherwise, in regions 2 and 3, the controller drives the various LED displays of display 88 to produce the display shown by element 300. As a result, the information appearing on the display 88 is always upright from the perspective of the operator, facilitating use of the display.

The installation and operation of the fluid injection system 1 will now be discussed. Prior to turning on the fluid injection system 1, a source of power 41, such as 110 or 220 volts of electricity sent through a line cord 43 from a wall socket (not shown), is provided to the fluid injection system 1. Thereafter, the operator turns on a master power switch (not shown), preferably situated on the power supply unit 39 of the fluid injection system 1. The fluid injection system 1 responds through visual indicia, such as the illumination of a green light (not shown) on the injector head 3, to indicate that the fluid injection system 1 has line power applied to the system power supply. The operator then turns on system power via a power switch (not shown) on the DCU 9. It is to be understood that the DCU 9 may be turned on automatically when the master power switch of the fluid injection system 1 is turned on. After power has been supplied to the DCU 9, the fluid injection system 1 responds by undergoing various self-diagnostic checks to determine if the fluid injection system 1 exhibits any faults or conditions that would prevent proper operation of the fluid injection system 1. If any of the self-diagnostic checks fail and/or a fault is detected in the fluid injection system 1, a critical error window or screen is displayed on DCU 9, which may instruct the operator to contact service personnel to remedy the fault or instruct the operator on how to remedy the fault himself or herself. Additionally, the fluid injection system 1 will not allow an operator to proceed with an injection if any of the self-diagnostic checks have failed. However, if all self-diagnostic checks are passed, the fluid injection system 1 proceeds to display a main control screen on the DCU 9.

Figure 41:
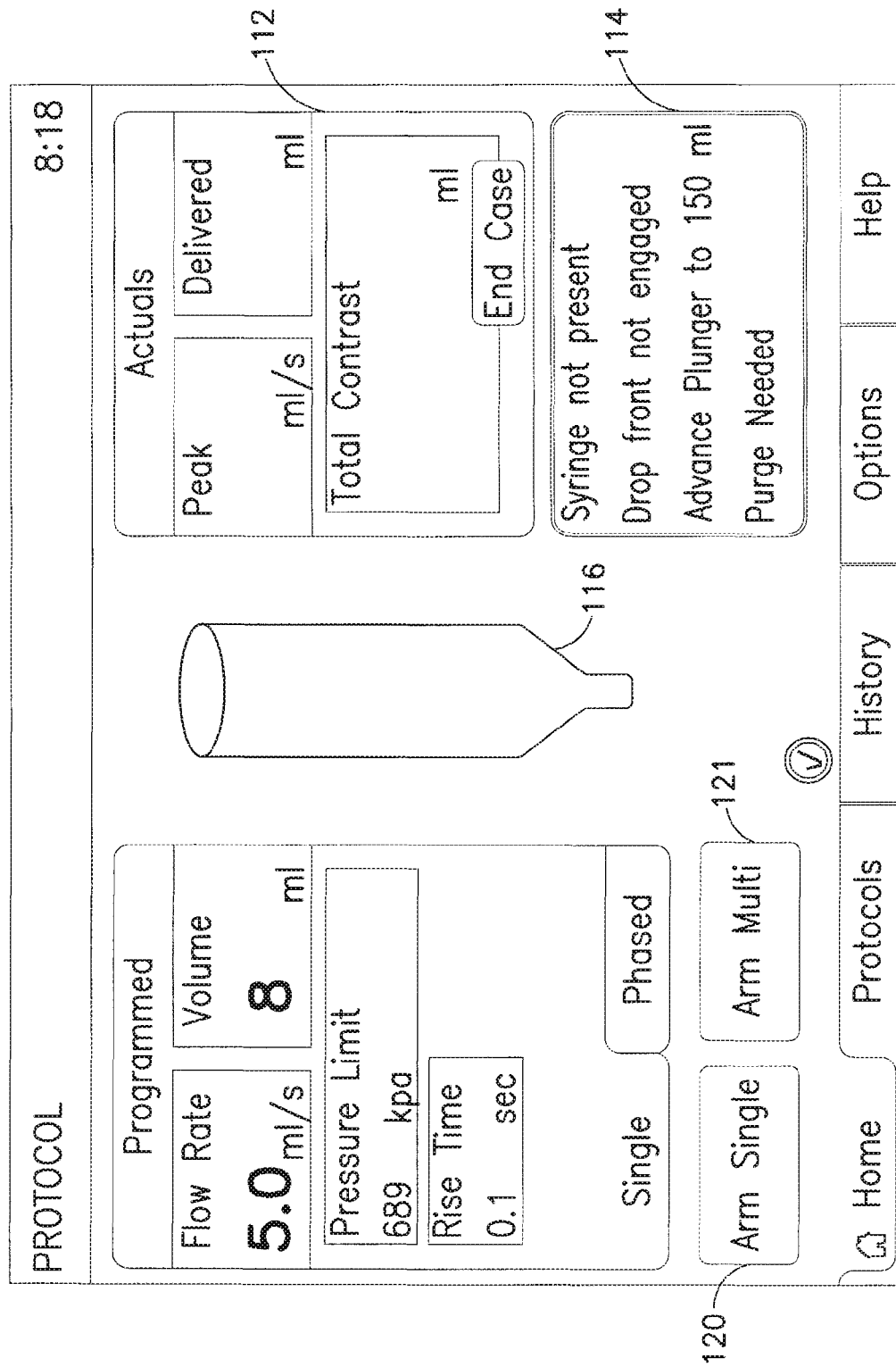
FIGS. 41 and 42 are respective graphical user interface displays presented to an operator during use of the fluid injection system in accordance with the device of the present disclosure.
Figure 42:
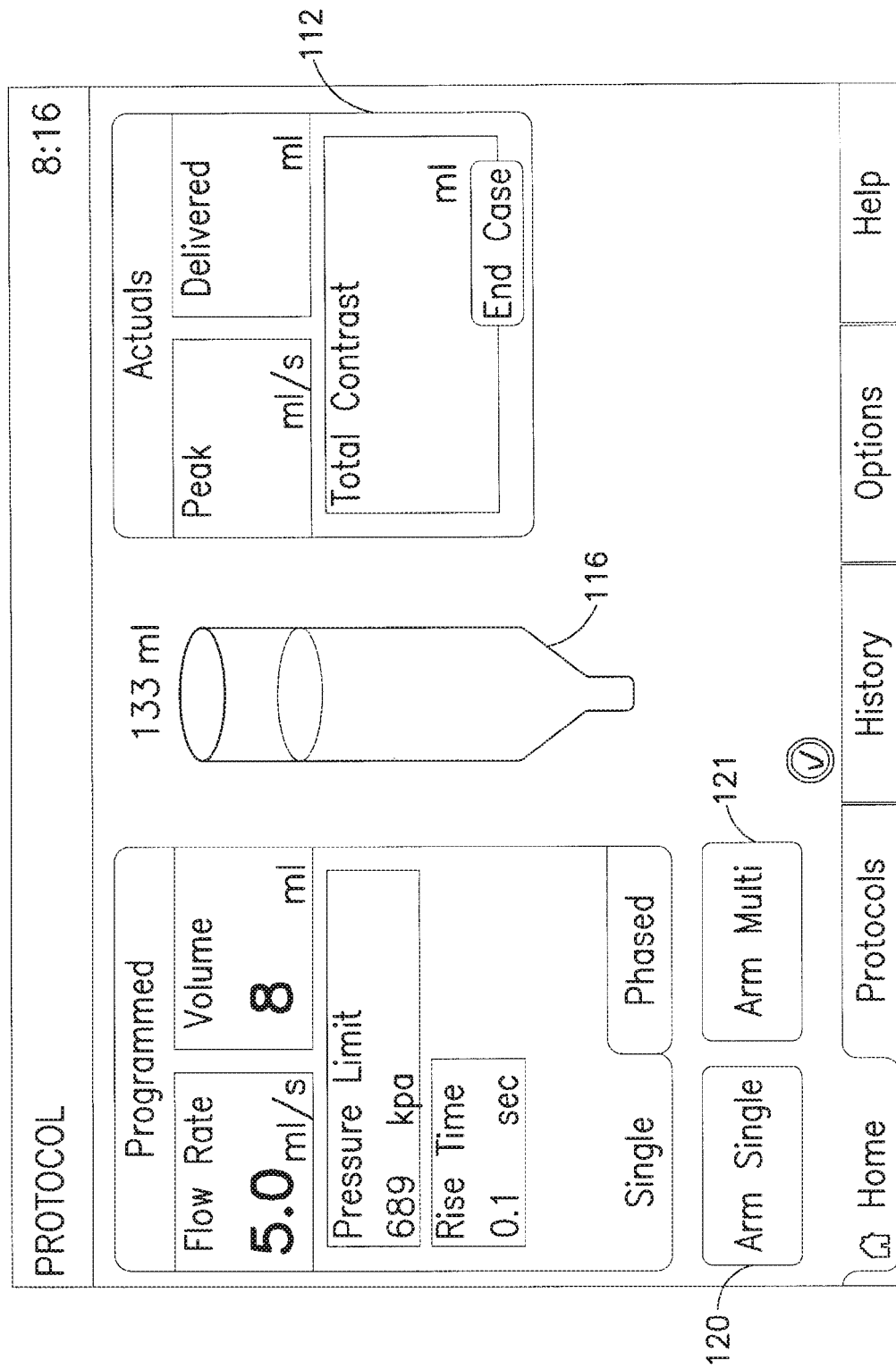

With reference to FIGS. 41 and 42, a main control screen 112 includes various on-screen controls, such as buttons, that may be accessed by the operator via the touch-screen graphical user interface of the DCU 9. The on-screen controls may include, but are not limited to, selectable options, menus, sub-menus, input fields, virtual keyboards, etc. The operator may therefore utilize the touch-screen of the DCU 9 to program one or more injection cycles of the fluid injection system 1 and to display performance parameters. It is to be understood that input to the DCU 9 may also be accomplished by providing an on-screen cursor and external pointing device, such as a trackball or mouse, that is operatively associated with the on-screen cursor. It is to be understood that the operator may stop any automatic functions of the fluid injection system 1 by touching an "Abort" button.

Once the fluid injection system 1 initializes, the user presses a "Continue" button (not shown) on the DCU 9. At this point, the main control screen 112 will include a "Smart Sentinel" box 114. The "Smart Sentinel" box 114 includes a list of actions on the main control screen 112 that must be completed by the operator before the injector head 3 can be armed to perform an injection procedure. This list of actions is based on input provided by one or all of the sensors positioned in the injector head 3 as described hereinabove. For instance, the list of actions may include load syringe, engage drop front, advance plunger, rotate injector head down to arm, rotate syringe and remove, disconnect patient, flow rate reduced, calibration needed, rotate head up and purge, injection complete, procedure halt—display touch, procedure halt—head touch, procedure halt—start switch, procedure halt—ISI, and procedure halt—low volume. However, this list is not to be construed as limiting the device of the present disclosure as it has been envisioned that a variety of other actions may be included in the "Smart Sentinel" box 114.

As discussed in greater detail hereinabove, the injector head 3 includes a variety of different sensors to provide a signal to the controller to determine if a syringe has been loaded, if the syringe retaining wall 83 has been properly positioned, if the plunger has been properly advanced, and/or the position of the injector head 3. Once a sensor provides a signal to the controller that the operator has completed an action from the list of actions, the action is removed from the list of actions on the DCU 9. Once all of the actions have been completed, the "Smart Sentinel" box 114 disappears as shown in FIG. 42 and the operator can arm the injector head 3. If any of the items remain in the "Smart Sentinel" box 114, the operator is prevented from arming the injector head 3 and an injection procedure cannot be performed. This feature has the advantage of adding clarity to the user interface and reducing interactions with the fluid injection system 1, increasing the likelihood that a user will have a successful interaction with the fluid injection system 1 and generate the desired outcome.

Returning to the operation of the fluid injection system 1, after the operator has reached the main control screen 112, the operator tilts the injector head 3 up so that it is in region 1, as discussed hereinabove. A syringe 61 is then installed by inserting the syringe into the pressure jacket 65 and raising the syringe support structure 69. Once the syringe is successfully installed, the listings of the notices to load the syringe and to engage the drop front of the syringe support structure 69 in the "Smart Sentinel" box 114 are automatically removed therefrom. In addition, the piston of the actuation system of the injector head 3 is then moved forward 150 mL to remove all air from the syringe 61. Once the piston has been advanced, the listing providing notice to advance the plunger in the "Smart Sentinel" box 114 is automatically removed therefrom, such that the only action remaining in the listing of actions in the "Smart Sentinel" box 114 is the notice to rotate the head down to arm.

The syringe 61 may now be initially filled with contrast media by removing the dust cap from the syringe 61 and installing a first end of a "quick fill" tube (not shown) on the syringe 61. A second end of the "quick fill" tube is inserted into an open contrast bottle (not shown) and the syringe 61 is filled. The syringe 61 may be filled automatically when the operator touches a "Fill Contrast" button on the DCU 9, which causes the fluid injection system 1 to enter an auto-fill mode. In the automatic fill mode, the fluid injection system 1 moves the injector piston proximally at a controlled rate, such as 3 mL/s, which causes contrast media to be drawn from the contrast bottle. The fluid injection system 1 may provide visual feedback of this action to the operator via the DCU 9, such as by an iconic representation 116 of the syringe 61 shown on main control screen 112. Thus, the fluid injection system 1 may display on the DCU 9 the current volume in the syringe 61 based upon the position of the injector piston. The fluid injection system 1 proceeds to draw contrast from the contrast bottle until a predetermined event occurs, such as when the total remaining volume in the syringe 61 reaches a preset or pre-chosen amount or the contrast media volume in the contrast container is depleted completely. Alternatively, the syringe 61 may be filled manually by retracting the injector piston using the control button 109 provided on the injector head 3.

Thereafter, the fluid injection system 1 is configured to undergo a purge of air from the filled syringe 61. This is accomplished by manually rotating the knob 90 to advance the injector piston, thereby purging any air remaining from the filled syringe 61. The operator may facilitate the removal of any remaining trapped air by tapping the body of the pressure jacket 65 and the syringe 61 to dislodge any air bubbles that may be stuck to the side of the syringe 61. It is to be understood that the purging operation may be repeated as necessary to ensure that all air is expelled from the syringe 61. Thereafter, the "quick fill" tube is removed and the dust cover is placed back on the syringe until it is ready for an injection procedure.

At this point, the fluid injection system 1 is ready to accept the installation of a disposable tubing set 118 (see FIG. 2). Specifically, the operator removes the dust cap from the syringe 61 and removes disposable tubing set 118 from its package. Then, the operator may secure the patient end of the disposable tubing set 118 to an examination table or other securing point. Thereafter, the operator connects the other end of the disposable tubing set 118 with the injection neck 77 of the syringe 61.

The operator then advances the injector piston by rotating the knob 90 to fill the disposable tubing set 118 with contrast from the syringe 61. The operator then rotates the injector head 3 downward until it reaches a position provided in region 3, as discussed hereinabove. Once the injector head 3 is rotated down, the listing of rotate head down to arm in the "Smart Sentinel" box 114 is automatically removed therefrom and the "Smart Sentinel" box 114 is removed from the main control screen, as shown in FIG. 42. In addition, an alert may be provided to the operator that all of the actions in the "Smart Sentinel" box 114 have been completed. This alert may be accomplished through either audio or visual indicia, such as a beep or an on-screen alert message, respectively. Thereafter, a wet-to-wet connection is performed by moving the knob 90 forward while connecting the patient end of the disposable tubing set 118 to the patient catheter.

Once the fluid injection system 1 is correctly connected to the patient, the operator enters the flow rate, volume, pressure (if necessary), and rise time (if necessary) for the injection procedure on the graphical user interface of the DCU 9. Alternatively, the fluid injection system 1 may maintain pre-programmed fluid delivery programs, (i.e., protocols), stored therein. Thus, instead of manually entering the desired flow rate, volume, pressure limit, and rise time for each injection cycle, the operator may program and store protocols, and recall previously stored protocols corresponding to injection elements, such as the desired flow rate, volume, pressure limit, and rise time. In an exemplary embodiment, a protocol is programmed and recalled via the on-screen controls of the DCU 9. After entering the appropriate values for a protocol, the operator may store the protocol into any available memory position of the fluid injection system 1 for future use of the protocol in other injection cycles with other patients. The operator may recall any previously stored protocol from the memory of the fluid injection system 1. In addition, the saved protocols may be sorted by date.

After the desired flow rate, volume, pressure, and rise time have been entered, either manually or automatically from a stored protocol, the operator arms the injector by pressing an appropriate "ARM" button 120 or 121 on the main control screen 112. This causes a pop up to appear on the main control screen 112 requesting a confirmation that all air has been expelled. Once the operator confirms that all air has been expelled, the fluid injection system 1 is armed. When ready, the operator initiates the injection by activating either the hand/foot switch 51 or, if the injector is connected to a scanner, ISI initiation. Upon initiation of the injection procedure, the injector piston moves forward, thereby causing the contrast media to flow until the programmed volume, as specified by the operator or the protocol, is delivered. The injector piston then ceases forward movement and the injection procedure is completed.

It is to be understood that the fluid injection system 1 may exist in either an armed or unarmed state, which corresponds respectively to whether or not the operator is allowed to perform an injection. The fluid injection system 1 may enter a disarmed or safe state when certain conditions are met including, but not limited to, failure of a self-diagnostic check, absence of some of the requisite components, and the reaching of a pressure limit that is deemed to be unsafe for the patient. The converse of these conditions and/or other factors must be present for the fluid injection system 1 to enter the armed state. The fluid injection system 1 may provide various visual and/or audible alarms to the operator to identify specific conditions that arise during the functioning of the fluid injection system 1. Such conditions may include, but are not limited to, the arming/disarming of the fluid injection system 1 and the state thereof and the reaching of a pressure disarm limit.

In addition, there are instances where it is desirable to use the fluid injection system 1 with high viscosity contrast agents and highly restrictive ID catheters (e.g., 4F OD and smaller). In such situations, the use of the fluid injection system 1 results in a significant amount of pressure in the disposable set (i.e., the catheter, syringe, etc.) at the end of the injection procedure. To cope with the pressure remaining at the end of an injection, the fluid injection system 1 described hereinabove monitors the pressure remaining and, when that pressure drops below a predetermined threshold value, executes an algorithm to remove the remaining pressure from the system. This is done in such a way as to minimize controlled recoil and maximize the amount of contrast delivered as a percentage of programmed volume.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure which is to be given the full breadth of the claims appended and any and all equivalents thereof.

The invention claimed is:

1. A fluid injection system comprising:
an injector head for delivering a fluid to a patient, the injector head comprising a housing, a mechanical interface on a front face of the housing for receiving a syringe, a piston positioned within the housing for connecting to a plunger of the syringe, and an actuation system positioned within the housing for moving the piston;
a plurality of temperature sensors positioned in the vicinity of the actuation system within the housing of the injector head for generating signals indicative of a temperature of the actuation system; and
a control system operationally coupled to the injector head and the at least one plurality of temperature sensors for controlling an injection procedure,
wherein the control system is configured to inhibit operation of the actuation system if the temperature determined by at least one temperature sensor of the plurality of temperature sensors exceeds a predefined threshold level.

2. The fluid injection system of claim 1, wherein the actuation system comprises: a gear train and linear ball screw; a brushless DC motor coupled to the gear train and linear ball screw; and a motor amplifier operationally coupled to the motor.

3. The fluid injection system of claim 1, wherein the control system is operationally coupled to a display unit having a graphical user interface.

4. The fluid injection system of claim 3, wherein a user is alerted that the temperature determined by at least one temperature sensor of the plurality of temperature sensors exceeds the predefined threshold level by a message appearing on the graphical user interface of the display unit.

5. The fluid injection system of claim 1, wherein the housing of the injector head further comprises a display on a top portion thereof.

6. The fluid injection system of claim 5, wherein the display displays information regarding at least one of the following: volume remaining, flow rate, pressure, and programmed volume.

7. A method of controlling a fluid injection system during a fluid injection procedure, the method comprising:
positioning a plurality of temperature sensors in a vicinity of an actuation system of an injector head of the fluid injection system;
receiving, by a control system of the fluid injection system, a signal indicative of a temperature of the actuation system from at least one temperature sensor of the plurality of temperature sensors; and
inhibiting, by the control system of the fluid injection system, operation of the actuation system if a temperature determined by at least one temperature sensor of the plurality of temperature sensors exceeds a predefined threshold level.

8. The method of claim 7, wherein the injector head is configured to deliver fluid to a patient and comprises a housing, a mechanical interface on a front face of the housing for receiving a syringe, a piston positioned within the housing for connecting to a plunger of the syringe, and the actuation system positioned within the housing for moving the piston.

9. The method of claim 7, wherein the actuation system comprises: a gear train and linear ball screw; a brushless DC motor coupled to the gear train and linear ball screw; and a motor amplifier operationally coupled to the motor.

10. The method of claim 7, further comprising:
alerting a user that the temperature determined by the at least one temperature sensor of the plurality of temperature sensors exceeds the predefined threshold level by a message appearing on a graphical user interface of a display unit that is operatively connected to the control system.

11. A fluid injection system comprising:
an injector head for delivering a fluid to a patient;
a reference plane sensor positioned on the injector head; and
a control system operationally coupled to the injector head and the reference plane sensor for controlling an injection procedure,
wherein the control system is configured to:
(a) receive an input from the reference plane sensor to establish a reference plane that is parallel to a floor surface;
(b) determine an existence of a reference plane offset detrimental to air management, wherein the reference plane offset is between the reference plane and the floor surface, by determining an existence of a sensor offset between a coordinate system of the reference plane sensor and an axis in a Cartesian system;
(c) alert a user in response to the existence of the reference plane offset that is detrimental to air management; and
(d) alert the user to reposition the injector head to a new reference plane to compensate for the reference plane offset thereby establishing the new reference plane which is parallel to the floor surface and corrects a detriment to air management.

12. The fluid injection system of claim 11, wherein the user is alerted of the existence of the reference plane offset between the reference plane and the floor surface by a message appearing on a graphical user interface of a display unit.

13. The fluid injection system of claim 11, wherein the reference plane sensor is a 3-axis accelerometer.

14. A fluid injection system comprising:
an injector head for delivering a fluid to a patient, the injector head comprising a housing, a mechanical interface on a front face of the housing for receiving at least one syringe, at least one piston positioned within the housing for connecting to a plunger of the at least one syringe, and an actuation system positioned within the housing for moving the at least one piston;
a reference plane sensor positioned on the injector head; and
a control system operationally coupled to the injector head and the reference plane sensor for controlling an injection procedure, wherein the control system is configured to:

receive an input from the reference plane sensor to establish a reference plane that is parallel to a floor surface;

determine an existence of a reference plane offset detrimental to air management, wherein the reference plane offset is between the reference plane and the floor surface, by determining an existence of a sensor offset between a coordinate system of the reference plane sensor and an axis in a Cartesian system;

alert a user in response to the existence of the reference plane offset that is detrimental to air management; and alert the user to reposition the injector head to a new reference plane to compensate for the reference plane offset thereby establishing the new reference plane which is parallel to the floor surface and corrects a detriment to air management.

15. The fluid injection system of claim 14, wherein the user is alerted of the existence of the offset between the reference plane and the floor surface by a message appearing on a graphical user interface of a display unit.

16. The fluid injection system of claim 14, wherein the reference plane sensor is a 3-axis accelerometer.

* * * * *

UNITED STATES PATENT AND TRADEMARK OFFICE
CERTIFICATE OF CORRECTION

PATENT NO. : 10,850,031 B2  
APPLICATION NO. : 16/013297  
DATED : December 1, 2020  
INVENTOR(S) : Shearer, Jr. et al.

Page 1 of 1

It is certified that error appears in the above-identified patent and that said Letters Patent is hereby corrected as shown below:

In the Specification  
In Column 20, Lines 46-47, delete "(from -10° to +55°, the" and insert -- (from -10° to +55°), the --, therefor.

In the Claims  
In Column 25, Line 30, in Claim 1, delete "and the at least one" and insert -- and --, therefor.

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*